(12) United States Patent
Artymiuk et al.

(10) Patent No.: US 8,273,552 B2
(45) Date of Patent: Sep. 25, 2012

(54) MODIFIED GROWTH HORMONE POLYPEPTIDES

(75) Inventors: Peter Artymiuk, Sheffield (GB); Richard Ross, Sheffield (GB); Jon Sayers, Chesterfield (GB)

(73) Assignee: Asterion Limited, Sheffield (GB)

( * ) Notice: Subject to any disclaimer, the term of this patent is extended or adjusted under 35 U.S.C. 154(b) by 151 days.

(21) Appl. No.: 12/678,282

(22) PCT Filed: Sep. 10, 2008

(86) PCT No.: PCT/GB2008/003056
§ 371 (c)(1),
(2), (4) Date: Mar. 15, 2010

(87) PCT Pub. No.: WO2009/047474
PCT Pub. Date: Apr. 16, 2009

(65) Prior Publication Data
US 2010/0197589 A1   Aug. 5, 2010

Related U.S. Application Data

(60) Provisional application No. 60/979,010, filed on Oct. 10, 2007.

(30) Foreign Application Priority Data

Oct. 11, 2007 (GB) .................................. 0719818.7

(51) Int. Cl.
*A61K 38/27* (2006.01)
*C07K 14/61* (2006.01)
*C12N 15/16* (2006.01)
*C12N 15/63* (2006.01)
*C12N 5/10* (2006.01)

(52) U.S. Cl. ..................... 435/69.4; 435/320.1; 435/325; 435/243; 514/11.3; 530/399

(58) Field of Classification Search .......................... None
See application file for complete search history.

(56) References Cited

FOREIGN PATENT DOCUMENTS

| EP | 2 100 955 A2 | 9/2009 |
|---|---|---|
| WO | WO 01/96565 A3 | 12/2001 |
| WO | WO 03/070765 A2 | 8/2003 |
| WO | WO 2004/090135 A2 | 10/2004 |
| WO | WO 2004/090135 A3 | 10/2004 |
| WO | WO 2009/013461 A8 | 1/2009 |

OTHER PUBLICATIONS

Database Accession No. ABK14535, "Human Fusion Protein cDNA GHlinkGHRflec," 2 pages (May 8, 2002).
Database Accession No. ADT77718, "Growth Hormone-GH Receptor + GPI Anchor Signal Coding Sequence," 2 pages (Jan. 13, 2005).
Database Accession No. AVA03164, "Human Growth Hormone/Receptor Fusion Gene, SEQ ID 1," 2 pages (Apr. 2, 2009).
Database Accession No. CQ895991, "Cytokine Polypeptides and Antibodies Containing a Signal Sequence for the Attachment of Glycosylphosphatidylinositol," 1 page (Nov. 5, 2004).
Database Accession No. HC000412, "Modified Linkers," 2 pages (Sep. 22, 2009).
International Search Report and Written Opinion from parent PCT Application No. PCT/GB2008/003056, 22 pages (mailed Jul. 15, 2010).
Kopchick and Okada, "Growth Hormone Receptor Antagonists: Discovery and Potential Uses," *Growth Hormone and IGF Research*, Supplement A, 11(1):S103-S109 (Jun. 1, 2001).
Parkinson and Trainer, "Pegvisomant: a Growth Hormone Receptor Antagonist for the Treatment of Acromegaly," *Growth Hormone and IGF Research*, Supplement B 10:S119-S123 (Apr. 1, 2004).
Pradhananga et al., "Tandem Fusions of Growth Hormone and its G120R Mutated Antagonist Retain Biological Activity and Demonstrate Prolonged Plasma Half-Life," *Growth Hormone and IGF Research* 14(2):116 (Apr. 1, 2004).

*Primary Examiner* — Christine J Saoud
(74) *Attorney, Agent, or Firm* — Klarquist Sparkman, LLP

(57) ABSTRACT

We describe modified growth hormone fusion proteins and dimers comprising said fusion proteins; nucleic acid molecules encoding said proteins and methods of treatment that use said proteins in the treatment of conditions that result from growth hormone excess.

22 Claims, 19 Drawing Sheets

Figure 1A
1B8v0 atggctacaggctcccggacgtccctgctcctggcttttggcctgctctgcctgccc
tggcttcaagagggcagtgccTTCCCAACCATTCCCTTATCCAGGCTTTTTGACAAC
GCTATGCTCCGCGCCCATCGTCTGCACCAGCTGGCCTTTGACACCTACCAGGAGTTT
GAAGAAGCCTATATCCCAAAGGAACAGAAGTATTCATTCCTGCAGAACCCCCAGACC
TCCCTCTGTTTCTCAGAGTCTATTCCGACACCCTCCAACAGGGAGGAAACACAACAG
AAATCCAACCTAGAGCTGCTCCGCATCTCCCTGCTGCTCATCCAGTCGTGGCTGGAG
CCCGTGCAGTTCCTCAGGAGTGTCTTCGCCAACAGCCTGGTGTACGGCGCCTCTGAC
AGCAACGTCTATGACCTCCTAAAGGACCTAGAGGAACGCATCCAAACGCTGATGGGG
AGGCTGGAAGATGGCAGCCCCCGGACTGGGCAGATCTTCAAGCAGACCTACAGCAAG
TTCGACACAAACTCACACAACGATGACGCACTACTCAAGAACTACGGGCTGCTCTAC
TGCTTCAGGAAGGACATGGACAAGGTCGAGACATTCCTGCGCATCGTGCAGTGCCGC
TCTGTGGAGGGCAGCTGTGGCTTCggcggccgcggtggcggaggtagtggtggcgga
ggtagcggtggcggaggttctggtggcggaggttccgaattcTTTTCTGGAAGTGAG
GCCACAGCAGCTATCCTTAGCAGAGCACCCTGGAGTCTGCAAAGTGTTAATCCAGGC
CTAAAGACAAATTCTTCTAAGGAGCCTAAATTCACCAAGTGCCGTTCACCTGAGCGA
GAGACTTTTTCATGCCACTGGACAGATGAGGTTCATCATGGTACAAAGAACCTAGGA
CCCATACAGCTGTTCTATACCAGAAGGAACACTCAAGAATGGACTCAAGAATGGAAA
GAATGCCCTGATTATGTTTCTGCTGGGGAAAACAGCTGTTACTTTAATTCATCGTTT
ACCTCCATCTGGATACCTTATTGTATCAAGCTAACTAGCAATGGTGGTACAGTGGAT
GAAAAGTGTTTCTCTGTTGATGAAATAGTGCAACCAGATCCACCCATTGCCCTCAAC
TGGACTTTACTGAACGTCAGTTTAACTGGGATTCATGCAGATATCCAAGTGAGATGG
GAAGCACCACGCAATGCAGATATTCAGAAAGGATGGATGGTTCTGGAGTATGAACTT
CAATACAAAGAAGTAAATGAAACTAAATGGAAAATGATGGACCCTATATTGACAACA
TCAGTTCCAGTGTACTCATTGAAAGTGGATAAGGAATATGAAGTACGCGTGAGATCC
AAACAACGAAACTCTGGAAATTATGGCGAGTTCAGTGAGGTGCTCTATGTAACACTT
CCTCAGATGAGCCAA AAGCTTTTCGAA*

Figure 1B

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFRKDMD
KVETFLRIVQCRSVEGSCGFGGRGGGGSGGGGSGGGGSGGGGSEFFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQKL
FE*

Figure 2A
1B8v1 atggctacaggctcccggacgtccctgctcctggcttttggcctgctctgcctgccc
tggcttcaagagggcagtgccTTCCCAACCATTCCCTTATCCAGGCTTTTTGACAAC
GCTATGCTCCGCGCCCATCGTCTGCACCAGCTGGCCTTTGACACCTACCAGGAGTTT
GAAGAAGCCTATATCCCAAAGGAACAGAAGTATTCATTCCTGCAGAACCCCCAGACC
TCCCTCTGTTTCTCAGAGTCTATTCCGACACCCTCCAACAGGGAGGAAACACAACAG
AAATCCAACCTAGAGCTGCTCCGCATCTCCCTGCTGCTCATCCAGTCGTGGCTGGAG
CCCGTGCAGTTCCTCAGGAGTGTCTTCGCCAACAGCCTGGTGTACGGCGCCTCTGAC
AGCAACGTCTATGACCTCCTAAAGGACCTAGAGGAACGCATCCAAACGCTGATGGGG
AGGCTGGAAGATGGCAGCCCCCGGACTGGGCAGATCTTCAAGCAGACCTACAGCAAG
TTCGACACAAACTCACACAACGATGACGCACTACTCAAGAACTACGGGCTGCTCTAC
TGCTTCAGGAAGGACATGGACAAGGTCGAGACATTCCTGCGCATCGTGCAGTGCCGC
TCTGTGGAGGGCAGCTGTGGCTTCggcggccgcggtggcggaggtagtggtggcgga
ggtagcggtggcggaggttctggtggcggaggttccgaattcTTTTCTGGAAGTGAG
GCCACAGCAGCTATCCTTAGCAGAGCACCCTGGAGTCTGCAAAGTGTTAATCCAGGC
CTAAAGACAAATTCTTCTAAGGAGCCTAAATTCACCAAGTGCCGTTCACCTGAGCGA
GAGACTTTTTCATGCCACTGGACAGATGAGGTTCATCATGGTACAAAGAACCTAGGA
CCCATACAGCTGTTCTATACCAGAAGGAACACTCAAGAATGGACTCAAGAATGGAAA
GAATGCCCTGATTATGTTTCTGCTGGGGAAAACAGCTGTTACTTTAATTCATCGTTT
ACCTCCATCTGGATACCTTATTGTATCAAGCTAACTAGCAATGGTGGTACAGTGGAT
GAAAAGTGTTTCTCTGTTGATGAAATAGTGCAACCAGATCCACCCATTGCCCTCAAC
TGGACTTTACTGAACGTCAGTTTAACTGGGATTCATGCAGATATCCAAGTGAGATGG
GAAGCACCACGCAATGCAGATATTCAGAAAGGATGGATGGTTCTGGAGTATGAACTT
CAATACAAAGAAGTAAATGAAACTAAATGGAAAATGATGGACCCTATATTGACAACA
TCAGTTCCAGTGTACTCATTGAAAGTGGATAAGGAATATGAAGTGCGTGTGAGATCC
AAACAACGAAACTCTGGAAATTATGGCGAGTTCAGTGAGGTGCTCTATGTAACACTT
CCTCAGATGAGCCAA*

Figure 2B

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLIQSWLEPVQFLRSVFANSLVYGASDSNVYDLL
KDLEERIQTLMGRLEDGSPRTGQIFKQTYSKFDTNSHNDDALLKNYGLLYCFRKDMD
KVETFLRIVQCRSVEGSCGFGGRGGGSGGGSGGGSGGGSEFFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ*

Figure 3A
1B8v2 atggctacaggctcccggacgtccctgctcctggcttttggcctgctctgcctgccc
tggcttcaagagggcagtgccTTCCCAACCATTCCCTTATCCAGGCTTTTTGACAAC
GCTATGCTCCGCGCCCATCGTCTGCACCAGCTGGCCTTTGACACCTACCAGGAGTTT
GAAGAAGCCTATATCCCAAAGGAACAGAAGTATTCATTCCTGCAGAACCCCCAGACC
TCCCTCTGTTTCTCAGAGTCTATTCCGACACCCTCCAACAGGGAGGAAACACAACAG
AAATCCAACCTAGAGCTGCTCCGCATCTCCCTGCTGCTCATCCAGTCGTGGCTGGAG
CCCGTGCAGTTCCTCAGGAGTGTCTTCGCCAACAGCCTGGTGTACGGCGCCTCTGAC
AGCAACGTCTATGACCTCCTAAAGGACCTAGAGGAACGCATCCAAACGCTGATGGGG
AGGCTGGAAGATGGCAGCCCCCGGACTGGGCAGATCTTCAAGCAGACCTACAGCAAG
TTCGACACAAACTCACACAACGATGACGCACTACTCAAGAACTACGGCTGCTCTAC
TGCTTCAGGAAGGACATGGACAAGGTCGAGACATTCCTGCGCATCGTGCAGTGCCGC
TCTGTGGAGGGCAGCTGTGGCTTCggtggcggaggtagtggtggcggaggtagcggt
ggcggaggttctggtggcggaggttccggtggcggaggtagtTTTTCTGGAAGTGAG
GCCACAGCAGCTATCCTTAGCAGAGCACCCTGGAGTCTGCAAAGTGTTAATCCAGGC
CTAAAGACAAATTCTTCTAAGGAGCCTAAATTCACCAAGTGCCGTTCACCTGAGCGA
GAGACTTTTTCATGCCACTGGACAGATGAGGTTCATCATGGTACAAAGAACCTAGGA
CCCATACAGCTGTTCTATACCAGAAGGAACACTCAAGAATGGACTCAAGAATGGAAA
GAATGCCCTGATTATGTTCTGCTGGGGAAAACAGCTGTTACTTTAATTCATCGTTT
ACCTCCATCTGGATACCTTATTGTATCAAGCTAACTAGCAATGGTGGTACAGTGGAT
GAAAAGTGTTTCTCTGTTGATGAAATAGTGCAACCAGATCCACCCATTGCCCTCAAC
TGGACTTTACTGAACGTCAGTTTAACTGGGATTCATGCAGATATCCAAGTGAGATGG
GAAGCACCACGCAATGCAGATATTCAGAAAGGATGGATGGTTCTGGAGTATGAACTT
CAATACAAAGAAGTAAATGAAACTAAATGGAAAATGATGGACCCTATATTGACAACA
TCAGTTCCAGTGTACTCATTGAAAGTGGATAAGGAATATGAAGTGCGTGTGAGATCC
AAACAACGAAACTCTGGAAATTATGGCGAGTTCAGTGAGGTGCTCTATGTAACACTT
CCTCAGATGAGCCAA*

Figure 3B

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFRKDMD
KVETFLRIVQCRSVEGSCGFGGGGSGGGGSGGGGSGGGGSGGGGSFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ*

Figure 4A
1B8v3

**atggctacaggctcccggacgtccctgctcctggcttttggcctgctctgcctgccc
tggcttcaagagggcagtgcc**TTCCCAACCATTCCCTTATCCAGGCTTTTTGACAAC
GCTATGCTCCGCGCCATCGTCTGCACCAGCTGGCCTTTGACACCTACCAGGAGTTT
GAAGAAGCCTATATCCCAAAGGAACAGAAGTATTCATTCCTGCAGAACCCCCAGACC
TCCCTCTGTTTCTCAGAGTCTATTCCGACACCCTCCAACAGGGAGGAAACACAACAG
AAATCCAACCTAGAGCTGCTCCGCATCTCCCTGCTGCTCATCCAGTCGTGGCTGGAG
CCCGTGCAGTTCCTCAGGAGTGTCTTCGCCAACAGCCTGGTGTACGGCGCCTCTGAC
AGCAACGTCTATGACCTCCTAAAGGACCTAGAGGAACGCATCCAAACGCTGATGGGG
AGGCTGGAAGATGGCAGCCCCGGACTGGGCAGATCTTCAAGCAGACCTACAGCAAG
TTCGACACAAACTCACACAACGATGACGCACTACTCAAGAACTACGGGCTGCTCTAC
TGCTTCAGGAAGGACATGGACAAGGTCGAGACATTCCTGCGCATCGTGCAGTGCCGC
TCTGTGGAGGGCAGCTGTGGCTTCTTTTCTGGAAGTGAGGCCACAGCAGCTATCCTT
AGCAGAGCACCCTGGAGTCTGCAAAGTGTTAATCCAGGCCTAAAGACAAATTCTTCT
AAGGAGCCTAAATTCACCAAGTGCCGTTCACCTGAGCGAGAGACTTTTCATGCCAC
TGGACAGATGAGGTTCATCATGGTACAAAGAACCTAGGACCCATACAGCTGTTCTAT
ACCAGAAGGAACACTCAAGAATGGACTCAAGAATGGAAAGAATGCCCTGATTATGTT
TCTGCTGGGGAAAACAGCTGTTACTTTAATTCATCGTTTACCTCCATCTGGATACCT
TATTGTATCAAGCTAACTAGCAATGGTGGTACAGTGGATGAAAAGTGTTTCTCTGTT
GATGAAATAGTGCAACCAGATCCACCCATTGCCCTCAACTGGACTTTACTGAACGTC
AGTTTAACTGGGATTCATGCAGATATCCAAGTGAGATGGGAAGCACCACGCAATGCA
GATATTCAGAAGGATGGATGGTTCTGGAGTATGAACTTCAATACAAAGAAGTAAAT
GAAACTAAATGGAAAATGATGGACCCTATATTGACAACATCAGTTCCAGTGTACTCA
TTGAAAGTGGATAAGGAATATGAAGTGCGTGTGAGATCCAAACAACGAAACTCTGGA
AATTATGGCGAGTTCAGTGAGGTGCTCTATGTAACACTTCCTCAGATGAGCCAA*

Figure 4B

MATGSRTSLLLAFGLLCLPWLQEGSA
FPTIPLSRLFDNAMLRAHRLHQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFRKDMD
KVETFLRIVQCRSVEGSCGFFSGSEATAAILSRAPWSLQSVNPGLKTNSSKEPKFTK
CRSPERETFSCHWTDEVHHGTKNLGPIQLFYTRRNTQEWTQEWKECPDYVSAGENSC
YFNSSFTSIWIPYCIKLTSNGGTVDEKCFSVDEIVQPDPPIALNWTLLNVSLTGIHA
DIQVRWEAPRNADIQKGWMVLEYELQYKEVNETKWKMMDPILTTSVPVYSLKVDKEY
EVRVRSKQRNSGNYGEFSEVLYVTLPQMSQ*

Figure 5A
1B9v0 atggctacaggctcccggacgtcctgctcctggcttttggcctgctctgcctgccc
tggcttcaagagggcagtgccTTCCCAACCATTCCCTTATCCAGGCTTTTTGACAAC
GCTATGCTCCGCGCCGACCGTCTGAACCAGCTGGCCTTTGACACCTACCAGGAGTTT
GAAGAAGCCTATATCCCAAAGGAACAGAAGTATTCATTCCTGCAGAACCCCCAGACC
TCCCTCTGTTTCTCAGAGTCTATTCCGACACCCTCCAACAGGGAGGAAACACAACAG
AAATCCAACCTAGAGCTGCTCCGCATCTCCCTGCTGCTCATCCAGTCGTGGCTGGAG
CCCGTGCAGTTCCTCAGGAGTGTCTTCGCCAACAGCCTGGTGTACGGCGCCTCTGAC
AGCAACGTCTATGACCTCCTAAAGGACCTAGAGGAACGCATCCAAACGCTGATGGGG
AGGCTGGAAGATGGCAGCCCCCGGACTGGGCAGATCTTCAAGCAGACCTACAGCAAG
TTCGACACAAACTCACACAACGATGACGCACTACTCAAGAACTACGGGCTGCTCTAC
TGCTTCAACGCCGACATGTCAAGGGTCTCAACATTCCTGCGCACAGTGCAGTGCCGC
TCTGTGGAGGGCAGCTGTGGCTTCggcggccgcggtggcggaggtagtggtggcgga
ggtagcggtggcggaggttctggtggcggaggttccgaattcTTTTCTGGAAGTGAG
GCCACAGCAGCTATCCTTAGCAGAGCACCCTGGAGTCTGCAAAGTGTTAATCCAGGC
CTAAAGACAAATTCTTCTAAGGAGCCTAAATTCACCAAGTGCCGTTCACCTGAGCGA
GAGACTTTTTCATGCCACTGGACAGATGAGGTTCATCATGGTACAAAGAACCTAGGA
CCCATACAGCTGTTCTATACCAGAAGGAACACTCAAGAATGGACTCAAGAATGGAAA
GAATGCCCTGATTATGTTTCTGCTGGGGAAAACAGCTGTTACTTTAATTCATCGTTT
ACCTCCATCTGGATACCTTATTGTATCAAGCTAACTAGCAATGGTGGTACAGTGGAT
GAAAAGTGTTTCTCTGTTGATGAAATAGTGCAACCAGATCCACCCATTGCCCTCAAC
TGGACTTTACTGAACGTCAGTTTAACTGGGATTCATGCAGATATCCAAGTGAGATGG
GAAGCACCACGCAATGCAGATATTCAGAAAGGATGGATGGTTCTGGAGTATGAACTT
CAATACAAAGAAGTAAATGAAACTAAATGGAAAATGATGGACCCTATATTGACAACA
TCAGTTCCAGTGTACTCATTGAAAGTGGATAAGGAATATGAAGTACGCGTGAGATCC
AAACAACGAAACTCTGGAAATTATGGCGAGTTCAGTGAGGTGCTCTATGTAACACTT
CCTCAGATGAGCCAA AAGCTTTTCGAA*

Figure 5B

MATGSRTSLLLAFGLLCLPWLQEGSA
FPTIPLSRLFDNAMLRADRLNQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFNADMS
RVSTFLRTVQCRSVEGSCGFGGRGGGGSGGGGSGGGGSGGGGSEFFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQKL
FE*

Figure 6A
1B9v1 atggctacaggctcccggacgtcctgctcctggcttttggcctgctctgcctgccc
tggcttcaagagggcagtgccTTCCCAACCATTCCCTTATCCAGGCTTTTGACAAC
GCTATGCTCCGCGCCGACCGTCTGAACCAGCTGGCCTTTGACACCTACCAGGAGTTT
GAAGAAGCCTATATCCCAAAGGAACAGAAGTATTCATTCCTGCAGAACCCCCAGACC
TCCCTCTGTTTCTCAGAGTCTATTCCGACACCCTCCAACAGGGAGGAAACACAACAG
AAATCCAACCTAGAGCTGCTCCGCATCTCCCTGCTGCTCATCCAGTCGTGGCTGGAG
CCCGTGCAGTTCCTCAGGAGTGTCTTCGCCAACAGCCTGGTGTACGGCGCCTCTGAC
AGCAACGTCTATGACCTCCTAAAGGACCTAGAGGAACGCATCCAAACGCTGATGGGG
AGGCTGGAAGATGGCAGCCCCGGACTGGGCAGATCTTCAAGCAGACCTACAGCAAG
TTCGACACAAACTCACACAACGATGACGCACTACTCAAGAACTACGGCTGCTCTAC
TGCTTCAACGCCGACATGTCAAGGGTCTCAACATTCCTGCGCACAGTGCAGTGCCGC
TCTGTGGAGGGCAGCTGTGGCTTCggcggccgcggtggcggaggtagtggtggcgga
ggtagcggtggcggaggttctggtggcggaggttccgaattcTTTTCTGGAAGTGAG
GCCACAGCAGCTATCCTTAGCAGAGCACCCTGGAGTCTGCAAAGTGTTAATCCAGGC
CTAAAGACAAATTCTTCTAAGGAGCCTAAATTCACCAAGTGCCGTTCACCTGAGCGA
GAGACTTTTTCATGCCACTGGACAGATGAGGTTCATCATGGTACAAAGAACCTAGGA
CCCATACAGCTGTTCTATACCAGAAGGAACACTCAAGAATGGACTCAAGAATGGAAA
GAATGCCCTGATTATGTTTCTGCTGGGGAAAACAGCTGTTACTTTAATTCATCGTTT
ACCTCCATCTGGATACCTTATTGTATCAAGCTAACTAGCAATGGTGGTACAGTGGAT
GAAAAGTGTTTCTCTGTTGATGAAATAGTGCAACCAGATCCACCCATTGCCCTCAAC
TGGACTTTACTGAACGTCAGTTTAACTGGGATTCATGCAGATATCCAAGTGAGATGG
GAAGCACCACGCAATGCAGATATTCAGAAAGGATGGATGGTTCTGGAGTATGAACTT
CAATACAAAGAAGTAAATGAAACTAAATGGAAAATGATGGACCCTATATTGACAACA
TCAGTTCCAGTGTACTCATTGAAAGTGGATAAGGAATATGAAGTGCGTGTGAGATCC
AAACAACGAAACTCTGGAAATTATGGCGAGTTCAGTGAGGTGCTCTATGTAACACTT
CCTCAGATGAGCCAA*

Figure 6B

MATGSRTSLLLAFGLLCLPWLQEGSA
FPTIPLSRLFDNAMLRADRLNQLAFDTYQEFEEAYIPKEQKYSFLQNPQTSLCFSES
IPTPSNREETQQKSNLELLRISLLIQSWLEPVQFLRSVFANSLVYGASDSNVYDLL
KDLEERIQTLMGRLEDGSPRTGQIFKQTYSKFDTNSHNDDALLKNYGLLYCFNADMS
RVSTFLRTVQCRSVEGSCGFGGRGGGGSGGGGSGGGGSGGGGSEFFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ*

Figure 7A
1B9v2 atggctacaggctcccggacgtccctgctcctggcttttggcctgctctgcctgccc
tggcttcaagagggcagtgccTTCCCAACCATTCCCTTATCCAGGCTTTTTGACAAC
GCTATGCTCCGCGCC`GAC`CGTCTG`AAC`CAGCTGGCCTTTGACACCTACCAGGAGTTT
GAAGAAGCCTATATCCCAAAGGAACAGAAGTATTCATTCCTGCAGAACCCCCAGACC
TCCCTCTGTTTCTCAGAGTCTATTCCGACACCCTCCAACAGGGAGGAAACACAACAG
AAATCCAACCTAGAGCTGCTCCGCATCTCCCTGCTGCTCATCCAGTCGTGGCTGGAG
CCCGTGCAGTTCCTCAGGAGTGTCTTCGCCAACAGCCTGGTGTACGGCGCCTCTGAC
AGCAACGTCTATGACCTCCTAAAGGACCTAGAGGAA`CGC`ATCCAAACGCTGATGGGG
AGGCTGGAAGATGGCAGCCCCGGACTGGGCAGATCTTCAAGCAGACCTACAGCAAG
TTCGACACAAACTCACACAACGATGACGCACTACTCAAGAACTACGGGCTGCTCTAC
TGCTTC`AACGCC`GACATG`TCAAGG`GTC`TCA`ACATTCTGCGC`ACA`GTGCAGTGCCGC
TCTGTGGAGGGCAGCTGTGGCTTCggtggcggaggtagtggtggcggaggtagcggt
ggcggaggttctggtggcggaggttccGgtggcggaggtagtTTTTCTGGAAGTGAG
GCCACAGCAGCTATCCTTAGCAGAGCACCCTGGAGTCTGCAAAGTGTTAATCCAGGC
CTAAAGACAAATTCTTCTAAGGAGCCTAAATTCACCAAGTGCCGTTCACCTGAGCGA
GAGACTTTTTCATGCCACTGGACAGATGAGGTTCATCATGGTACAAAGAACCTAGGA
CCCATACAGCTGTTCTATACCAGAAGGAACACTCAAGAATGGACTCAAGAATGGAAA
GAATGCCCTGATTATGTTTCTGCTGGGGAAAACAGCTGTTACTTTAATTCATCGTTT
ACCTCCATCTGGATACCTTATTGTATCAAGCTAACTAGCAATGGTGGTACAGTGGAT
GAAAAGTGTTTCTCTGTTGATGAAATAGTGCAACCAGATCCACCCATTGCCCTCAAC
TGGACTTTACTGAACGTCAGTTTAACTGGGATTCATGCAGATATCCAAGTGAGATGG
GAAGCACCACGCAATGCAGATATTCAGAAGGATGGATGGTTCTGGAGTATGAACTT
CAATACAAAGAAGTAAATGAAACTAAATGGAAAATGATGGACCCTATATTGACAACA
TCAGTTCCAGTGTACTCATTGAAAGTGGATAAGGAATATGAAGTGCGTGTGAGATCC
AAACAACGAAACTCTGGAAATTATGGCGAGTTCAGTGAGGTGCTCTATGTAACACTT
CCTCAGATGAGCCAA*

Figure 7B

MATGSRTSLLLAFGLLCLPWLQEGSA
FPTIPLSRLFDNAMLRADRLNQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFNADMS
RVSTFLRTVQCRSVEGSCGFGGGGSGGGGSGGGGSGGGGSFSGSEATAAILS
RAPWSLQSVNPGLKTNSSKEPKFTKCRSPERETFSCHWTDEVHHGTKNLGPIQLFYT
RRNTQEWTQEWKECPDYVSAGENSCYFNSSFTSIWIPYCIKLTSNGGTVDEKCFSVD
EIVQPDPPIALNWTLLNVSLTGIHADIQVRWEAPRNADIQKGWMVLEYELQYKEVNE
TKWKMMDPILTTSVPVYSLKVDKEYEVRVRSKQRNSGNYGEFSEVLYVTLPQMSQ*

Figure 8A
1B9v3 atggctacaggctcccggacgtccctgctcctggcttttggcctgctctgcctgccc
tggcttcaagagggcagtgccTTCCCAACCATTCCCTTATCCAGGCTTTTTGACAAC
GCTATGCTCCGCGCCGACCGTCTGAACCAGCTGGCCTTTGACACCTACCAGGAGTTT
GAAGAAGCCTATATCCCAAAGGAACAGAAGTATTCATTCCTGCAGAACCCCCAGACC
TCCCTCTGTTTCTCAGAGTCTATTCCGACACCCTCCAACAGGGAGGAAACACAACAG
AAATCCAACCTAGAGCTGCTCCGCATCTCCCTGCTGCTCATCCAGTCGTGGCTGGAG
CCCGTGCAGTTCCTCAGGAGTGTCTTCGCCAACAGCCTGGTGTACGGCGCCTCTGAC
AGCAACGTCTATGACCTCCTAAAGGACCTAGAGGAACGCATCCAAACGCTGATGGGG
AGGCTGGAAGATGGCAGCCCCGGACTGGGCAGATCTTCAAGCAGACCTACAGCAAG
TTCGACACAAACTCACACAACGATGACGCACTACTCAAGAACTACGGGCTGCTCTAC
TGCTTCAACGCCGACATGTCAAGGGTCTCAACATTCCTGCGCACAGTGCAGTGCCGC
TCTGTGGAGGGCAGCTGTGGCTTCTTTTCTGGAAGTGAGGCCACAGCAGCTATCCTT
AGCAGAGCACCCTGGAGTCTGCAAAGTGTTAATCCAGGCCTAAAGACAAATTCTTCT
AAGGAGCCTAAATTCACCAAGTGCCGTTCACCTGAGCGAGAGACTTTTTCATGCCAC
TGGACAGATGAGGTTCATCATGGTACAAAGAACCTAGGACCCATACAGCTGTTCTAT
ACCAGAAGGAACACTCAAGAATGGACTCAAGAATGGAAAGAATGCCCTGATTATGTT
TCTGCTGGGGAAAACAGCTGTTACTTTAATTCATCGTTTACCTCCATCTGGATACCT
TATTGTATCAAGCTAACTAGCAATGGTGGTACAGTGGATGAAAGTGTTTCTCTGTT
GATGAAATAGTGCAACCAGATCCACCCATTGCCCTCAACTGGACTTTACTGAACGTC
AGTTTAACTGGGATTCATGCAGATATCCAAGTGAGATGGGAAGCACCACGCAATGCA
GATATTCAGAAAGGATGGATGGTTCTGGAGTATGAACTTCAATACAAAGAAGTAAAT
GAAACTAAATGGAAAATGATGGACCCTATATTGACAACATCAGTTCCAGTGTACTCA
TTGAAAGTGGATAAGGAATATGAAGTGCGTGTGAGATCCAAACAACGAAACTCTGGA
AATTATGGCGAGTTCAGTGAGGTGCTCTATGTAACACTTCCTCAGATGAGCCAA*

Figure 8B

MATGSRTSLLLAFGLLCLPWLQEGSA
FPTIPLSRLFDNAMLRADRLNQLAFDTYQEFEEAYIPKEQKYSFLQNPQTSLCFSES
IPTPSNREETQQKSNLELLRISLLLIQSWLEPVQFLRSVFANSLVYGASDSNVYDLL
KDLEERIQTLMGRLEDGSPRTGQIFKQTYSKFDTNSHNDDALLKNYGLLYCFNADMS
RVSTFLRTVQCRSVEGSCGFFSGSEATAAILSRAPWSLQSVNPGLKTNSSKEPKFTK
CRSPERETFSCHWTDEVHHGTKNLGPIQLFYTRRNTQEWTQEWKECPDYVSAGENSC
YFNSSFTSIWIPYCIKLTSNGGTVDEKCFSVDEIVQPDPPIALNWTLLNVSLTGIHA
DIQVRWEAPRNADIQKGWMVLEYELQYKEVNETKWKMMDPILTTSVPVYSLKVDKEY
EVRVRSKQRNSGNYGEFSEVLYVTLPQMSQ*

Figure 11

GGCGCCTCTGACAGCAACGTCTATGACCTCCTAAAGGACCTAGAGGAACGC
ATCCAAACGCTGATGGGGAGGCTGGAAGATGGCAGCCCCGGACTGGGCA
GATCTTCAAGCAGACCTACAGCAAGTTCGACACAAACTCACACAACGATGA
CGCACTACTCAAGAACTACGGGCTGCTCTACTGCTTCAGGAAGGACATGGA
CAAGGTCGAGACATTCCTGCGCATCGTGCAGTGCCGCTCTGTGGAGGGCA
GCTGTGGCTTCGGTGGCGGAGGTAGTGGTGGCGGAGGTAGCGGTGGCGG
AGGTTCTGGTGGCGGAGGTTCCGGTGGCGGAGGTAGTTTTTCTGGAAGTG
AGGCCACAGCAGCTATCCTTAGCAGAGCACCCTGGAGTCTGCAAAGTGTTA
ATCCAGGCCTAAAGACAAATTCTTCTAAGGAGCCTAAATTCACCAAGTGCCG
TTCACCTGAGCGAGAGACTTTTTCATGCCACTGGACAGATGAGGTTCATCAT
GGTACAAAGAACCTAGG

Figure 12

GGCGCCTCTGACAGCAACGTCTATGACCTCCTAAAGGACCTAGAGGAACG
CATCCAAACGCTGATGGGGAGGCTGGAAGATGGCAGCCCCGGACTGGG
CAGATCTTCAAGCAGACCTACAGCAAGTTCGACACAAACTCACACAACGAT
GACGCACTACTCAAGAACTACGGGCTGCTCTACTGCTTCAACGCCGACATG
TCAAGGGTCTCAACATTCCTGCGCACAGTGCAGTGCCGCTCTGTGGAGGG
CAGCTGTGGCTTCGGTGGCGGAGGTAGTGGTGGCGGAGGTAGCGGTGG
CGGAGGTTCTGGTGGCGGAGGTTCCGGTGGCGGAGGTAGTTTTTCTGGA
AGTGAGGCCACAGCAGCTATCCTTAGCAGAGCACCCTGGAGTCTGCAAAG
TGTTAATCCAGGCCTAAAGACAAATTCTTCTAAGGAGCCTAAATTCACCAAG
TGCCGTTCACCTGAGCGAGAGACTTTTTCATGCCACTGGACAGATGAGGTT
CATCATGGTACAAAGAACCTAGG

SDS-PAGE: 2 µg/lane

1. SeeBluePlus2
2. 1B8v2 Load
3. Unbound
4. Wash
5. E1
6. E2
7. E3
8. E4
9. E5
10. E6

SDS-PAGE: 2 µg/lane

1. SeeBluePlus2
2. 1B9v2 Load
3. Unbound
4. Wash
5. D1
6. D2
7. D3
8. D4
9. D5
10. D6

Figure 20A

|  | [protein] (µg/ml) | Volume (ml) | Total protein (mg) |
|---|---|---|---|
| 1B8v2 load | 293 | 106 | 31.1 |
| Unbound | 227 | 120 | 27.2 |
| Wash | - | 120 | - |
| Elution 1 | - | 5 | - |
| Elution 2 | 60.7 | 5 | 0.3 |
| Elution 3 | 63.6 | 5 | 0.32 |
| Elution 4 | 84.7 | 5 | 0.42 |
| Elution 5 | 18.5 | 5 | 0.09 |
| Elution 6 | 10.0 | 5 | 0.05 |
| 30kDa F/T | 8.6 | 450 | 3.9 |

Figure 20B

|  | [protein] (µg/ml) | Volume (ml) | Total protein (mg) |
|---|---|---|---|
| 1B9v2 load | 311 | 110 | 34.2 |
| Unbound | 246 | 125 | 30.8 |
| Wash | - | 150 | - |
| Elution 1 | 9.4 | 5 | - |
| Elution 2 | 32.4 | 5 | 0.16 |
| Elution 3 | 129 | 5 | 0.65 |
| Elution 4 | 80.1 | 5 | 0.4 |
| Elution 5 | 37.1 | 5 | 0.19 |
| Elution 6 | 9.4 | 5 | 0.05 |
| 30kDa F/T | 9.4 | 450 |  |

SEQUENCE LISTING

```
<160> NUMBER OF SEQ ID NOS: 32

<210> SEQ ID NO 1
<211> LENGTH: 1452
<212> TYPE: DNA
<213> ORGANISM: Artificial
<220> FEATURE:
<223> OTHER INFORMATION: growth hormone fusion protein

<400> SEQUENCE: 1
atggctacag gctcccggac gtccctgctc ctggcttttg gcctgctctg cctgccctgg      60
cttcaagagg gcagtgcctt cccaaccatt cccttatcca ggcttttga caacgctatg     120 ctccgcgccc atcgtctgca ccagctggcc tttgacacct accaggagtt tgaagaagcc     180
tatatcccaa aggaacagaa gtattcattc ctgcagaacc cccagacctc cctctgtttc     240
tcagagtcta ttccgacacc ctccaacagg gaggaaacac aacagaaatc caacctagag     300
ctgctccgca tctccctgct gctcatccag tcgtggctgg agcccgtgca gttcctcagg     360
```

| | |
|---|---|
| agtgtcttcg ccaacagcct ggtgtacggc gcctctgaca gcaacgtcta tgacctccta | 420 |
| aaggacctag aggaacgcat ccaaacgctg atggggaggc tggaagatgg cagccccgg | 480 |
| actgggcaga tcttcaagca gacctacagc aagttcgaca caaactcaca caacgatgac | 540 |
| gcactactca agaactacgg gctgctctac tgcttcagga aggacatgga caaggtcgag | 600 |
| acattcctgc gcatcgtgca gtgccgctct gtggagggca gctgtggctt cggcggccgc | 660 |
| ggtggcggag gtagtggtgg cggaggtagc ggtggcggag gttctggtgg cggaggttcc | 720 |
| gaattctttt ctggaagtga ggccacagca gctatcctta gcagagcacc ctggagtctg | 780 |
| caaagtgtta atccaggcct aaagacaaat tcttctaagg agcctaaatt caccaagtgc | 840 |
| cgttcacctg agcgagagac ttttcatgc cactggacag atgaggttca tcatggtaca | 900 |
| aagaacctag acccataca gctgttctat accagaagga acactcaaga atggactcaa | 960 |
| gaatggaaag aatgccctga ttatgtttct gctggggaaa acagctgtta ctttaattca | 1020 |
| tcgtttacct ccatctggat accttattgt atcaagctaa ctagcaatgg tggtacagtg | 1080 |
| gatgaaaagt gtttctctgt tgatgaaata gtgcaaccag atccacccat tgccctcaac | 1140 |
| tggactttac tgaacgtcag tttaactggg attcatgcag atatccaagt gagatgggaa | 1200 |
| gcaccacgca atgcagatat tcagaaagga tggatggttc tggagtatga acttcaatac | 1260 |
| aaagaagtaa atgaaactaa atggaaaatg atggaccta tattgacaac atcagttcca | 1320 |
| gtgtactcat tgaaagtgga taaggaatat gaagtacgcg tgagatccaa caacgaaac | 1380 |
| tctggaaatt atggcgagtt cagtgaggtg ctctatgtaa cacttcctca gatgagccaa | 1440 |
| aagcttttcg aa | 1452 |

<210> SEQ ID NO 2
<211> LENGTH: 1374
<212> TYPE: DNA
<213> ORGANISM: Artificial
<220> FEATURE:
<223> OTHER INFORMATION: growth hormone fusion protein

<400> SEQUENCE: 2

| | |
|---|---|
| ttcccaacca ttcccttatc caggcttttt gacaacgcta tgctccgcgc ccatcgtctg | 60 |
| caccagctgg cctttgacac ctaccaggag tttgaagaag cctatatccc aaaggaacag | 120 |
| aagtattcat tcctgcagaa cccccagacc tccctctgtt tctcagagtc tattccgaca | 180 |
| ccctccaaca gggaggaaac acaacagaaa tccaacctag agctgctccg catctccctg | 240 |
| ctgctcatcc agtcgtggct ggagcccgtg cagttcctca ggagtgtctt cgccaacagc | 300 |
| ctggtgtacg gcgcctctga cagcaacgtc tatgacctcc taaggaccct agaggaacgc | 360 |
| atccaaacgc tgatggggag gctggaagat ggcagccccc ggactgggca gatcttcaag | 420 |
| cagacctaca gcaagttcga cacaaactca cacaacgatg acgcactact caagaactac | 480 |
| gggctgctct actgcttcag gaaggacatg gacaaggtcg agacattcct gcgcatcgtg | 540 |
| cagtgccgct ctgtggaggg cagctgtggc ttcggcggcc gcggtggcgg aggtagtggt | 600 |
| ggcggaggta gcggtggcgg aggttctggt ggcggaggtt ccgaattctt ttctggaagt | 660 |
| gaggccacag cagctatcct tagcagagca ccctggagtc tgcaaagtgt taatccaggc | 720 |
| ctaaagacaa attcttctaa ggagcctaaa ttcaccaagt gccgttcacc tgagcgagag | 780 |
| acttttttcat gccactggac agatgaggtt catcatggta caagaaacct aggacccata | 840 |
| cagctgttct ataccagaag gaacactcaa gaatggactc aagaatggaa agaatgccct | 900 |
| gattatgttt ctgctgggga aaacagctgt tactttaatt catcgtttac ctccatctgg | 960 |

-continued

```
ataccttatt gtatcaagct aactagcaat ggtggtacag tggatgaaaa gtgtttctct    1020
gttgatgaaa tagtgcaacc agatccaccc attgccctca actggacttt actgaacgtc    1080
agtttaactg ggattcatgc agatatccaa gtgagatggg aagcaccacg caatgcagat    1140
attcagaaag gatggatggt tctggagtat gaacttcaat acaaagaagt aaatgaaact    1200
aaatggaaaa tgatggaccc tatattgaca acatcagttc cagtgtactc attgaaagtg    1260
gataaggaat atgaagtacg cgtgagatcc aaacaacgaa actctggaaa ttatggcgag    1320
ttcagtgagg tgctctatgt aacacttcct cagatgagcc aaaagctttt cgaa          1374
```

```
<210> SEQ ID NO 3
<211> LENGTH: 458
<212> TYPE: PRT
<213> ORGANISM: Artificial
<220> FEATURE:
<223> OTHER INFORMATION: growth hormone fusion protein

<400> SEQUENCE: 3

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Arg Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Gly
            180                 185                 190

Gly Arg Gly Gly Gly Ser Gly Gly Gly Ser Gly Gly Gly
        195                 200                 205

Ser Gly Gly Gly Ser Glu Phe Phe Ser Gly Ser Glu Ala Thr Ala
    210                 215                 220

Ala Ile Leu Ser Arg Ala Pro Trp Ser Leu Gln Ser Val Asn Pro Gly
225                 230                 235                 240

Leu Lys Thr Asn Ser Ser Lys Glu Pro Lys Phe Thr Lys Cys Arg Ser
                245                 250                 255

Pro Glu Arg Glu Thr Phe Ser Cys His Trp Thr Asp Glu Val His His
            260                 265                 270

Gly Thr Lys Asn Leu Gly Pro Ile Gln Leu Phe Tyr Thr Arg Arg Asn
        275                 280                 285

Thr Gln Glu Trp Thr Gln Glu Trp Lys Glu Cys Pro Asp Tyr Val Ser
    290                 295                 300
```

```
Ala Gly Glu Asn Ser Cys Tyr Phe Asn Ser Ser Phe Thr Ser Ile Trp
305                 310                 315                 320

Ile Pro Tyr Cys Ile Lys Leu Thr Ser Asn Gly Gly Thr Val Asp Glu
            325                 330                 335

Lys Cys Phe Ser Val Asp Glu Ile Val Gln Pro Asp Pro Pro Ile Ala
        340                 345                 350

Leu Asn Trp Thr Leu Leu Asn Val Ser Leu Thr Gly Ile His Ala Asp
    355                 360                 365

Ile Gln Val Arg Trp Glu Ala Pro Arg Asn Ala Asp Ile Gln Lys Gly
370                 375                 380

Trp Met Val Leu Glu Tyr Glu Leu Gln Tyr Lys Glu Val Asn Glu Thr
385                 390                 395                 400

Lys Trp Lys Met Met Asp Pro Ile Leu Thr Thr Ser Val Pro Val Tyr
            405                 410                 415

Ser Leu Lys Val Asp Lys Glu Tyr Glu Val Arg Val Arg Ser Lys Gln
        420                 425                 430

Arg Asn Ser Gly Asn Tyr Gly Glu Phe Ser Glu Val Leu Tyr Val Thr
    435                 440                 445

Leu Pro Gln Met Ser Gln Lys Leu Phe Glu
    450                 455

<210> SEQ ID NO 4
<211> LENGTH: 1440
<212> TYPE: DNA
<213> ORGANISM: Artificial
<220> FEATURE:
<223> OTHER INFORMATION: growth hormone fusion protein

<400> SEQUENCE: 4
atggctacag gctcccggac gtccctgctc ctggcttttg cctgctctg cctgccctgg      60 cttcaagagg gcagtgcctt cccaaccatt cccttatcca ggcttttga caacgctatg     120 ctccgcgccc atcgtctgca ccagctggcc tttgacacct accaggagtt tgaagaagcc     180
tatatcccaa aggaacagaa gtattcattc ctgcagaacc cccagacctc cctctgtttc     240
tcagagtcta ttccgacacc ctccaacagg gaggaaacac aacagaaatc caacctagag     300
ctgctccgca tctccctgct gctcatccag tcgtggctgg agcccgtgca gttcctcagg     360
agtgtcttcg ccaacagcct ggtgtacggc gcctctgaca gcaacgtcta tgacctccta     420
aaggacctag aggaacgcat ccaaacgctg atggggaggc tggaagatgg cagccccggg     480
actgggcaga tcttcaagca gacctacagc aagttcgaca caaactcaca caacgatgac     540
gcactactca gaactacggg ctgctctac tgcttcagga aggacatgga caaggtcgag     600
acattcctgc gatcgtgca gtgccgctct gtggagggca gctgtggctt cggcggccgc     660
ggtggcggag gtagtggtgg cggaggtagc ggtggcggag gttctggtgg cggaggttcc     720
gaattctttt ctggaagtga ggccacagca gctatcctta gcagagcacc ctggagtctg     780
caaagtgtta atccaggcct aaagacaaat tcttctaagg agcctaaatt caccaagtgc     840
cgttcacctg agcgagagac ttttcatgc cactggacag atgaggttca tcatggtaca     900
aagaacctag acccataca gctgttctat accagaagga acactcaaga atggactcaa     960
gaatggaaag aatgccctga ttatgtttct gctggggaaa acagctgtta ctttaattca    1020
tcgtttacct ccatctggat accttattgt atcaagctaa ctagcaatgg tggtacagtg    1080
gatgaaaagt gtttctctgt tgatgaaata gtgcaaccag atccaccat gccctcaac    1140 tggactttac tgaacgtcag tttaactggg attcatgcag atatccaagt gagatgggaa    1200
```

```
gcaccacgca atgcagatat tcagaaagga tggatggttc tggagtatga acttcaatac    1260
aaagaagtaa atgaaactaa atggaaaatg atggacccta tattgacaac atcagttcca    1320
gtgtactcat tgaaagtgga taaggaatat gaagtgcgtg tgagatccaa acaacgaaac    1380
tctggaaatt atggcgagtt cagtgaggtg ctctatgtaa cacttcctca gatgagccaa    1440
```

<210> SEQ ID NO 5
<211> LENGTH: 1362
<212> TYPE: DNA
<213> ORGANISM: Artificial
<220> FEATURE:
<223> OTHER INFORMATION: growth hormone fusion protein

<400> SEQUENCE: 5

```
ttcccaacca ttcccttatc caggcttttt gacaacgcta tgctccgcgc ccatcgtctg      60
caccagctgg cctttgacac ctaccaggag tttgaagaag cctatatccc aaaggaacag     120
aagtattcat tcctgcagaa ccccagacc tccctctgtt tctcagagtc tattccgaca     180
ccctccaaca gggaggaaac acaacagaaa tccaacctag agctgctccg catctccctg     240
ctgctcatcc agtcgtggct ggagcccgtg cagttcctca ggagtgtctt cgccaacagc     300
ctggtgtacg gcgcctctga cagcaacgtc tatgacctcc taaggaccct agaggaacgc     360
atccaaacgc tgatggggag gctggaagat ggcagccccc ggactgggca gatcttcaag     420
cagacctaca gcaagttcga cacaaactca cacaacgatg acgcactact caagaactac     480
gggctgctct actgcttcag gaaggacatg gacaaggtcg agacattcct gcgcatcgtg     540
cagtgccgct ctgtggaggg cagctgtggc ttcggcggcc gcggtggcgg aggtagtggt     600
ggcggaggta gcggtggcgg aggttctggt ggcggaggtt ccgaattctt ttctggaagt     660
gaggccacag cagctatcct tagcagagca ccctggagtc tgcaaagtgt taatccaggc     720
ctaaagacaa attcttctaa ggagcctaaa ttcaccaagt gccgttcacc tgagcgagag     780 acttttcat gccactggac agatgaggtt catcatggta caaagaacct aggacccata     840
cagctgttct ataccagaag gaacactcaa gaatggactc aagaatggaa agaatgccct     900
gattatgttt ctgctgggga aaacagctgt tactttaatt catcgtttac ctccatctgg     960
ataccttatt gtatcaagct aactagcaat ggtggtacag tggatgaaaa gtgtttctct    1020
gttgatgaaa tagtgcaacc agatccaccc attgccctca actggactt actgaacgtc    1080 agtttaactg ggattcatgc agatatccaa gtgagatggg aagcaccacg caatgcagat    1140
attcagaaag gatggatggt tctggagtat gaacttcaat acaaagaagt aaatgaaact    1200
aaatggaaaa tgatggaccc tatattgaca acatcagttc cagtgtactc attgaaagtg    1260
gataaggaat atgaagtgcg tgtgagatcc aaacaacgaa actctggaaa ttatggcgag    1320
ttcagtgagg tgctctatgt aacacttcct cagatgagcc aa                      1362
```

<210> SEQ ID NO 6
<211> LENGTH: 454
<212> TYPE: PRT
<213> ORGANISM: Artificial
<220> FEATURE:
<223> OTHER INFORMATION: growth hormone fusion protein

<400> SEQUENCE: 6

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30
```

-continued

```
Glu Ala Tyr Ile Pro Lys Glu Gln Lys Tyr Ser Phe Leu Gln Asn Pro
         35                  40                  45
Gln Thr Ser Leu Cys Phe Ser Glu Ser Ile Pro Thr Pro Ser Asn Arg
 50                  55                  60
Glu Glu Thr Gln Gln Lys Ser Asn Leu Glu Leu Leu Arg Ile Ser Leu
 65                  70                  75                  80
Leu Leu Ile Gln Ser Trp Leu Glu Pro Val Gln Phe Leu Arg Ser Val
                 85                  90                  95
Phe Ala Asn Ser Leu Val Tyr Gly Ala Ser Asp Ser Asn Val Tyr Asp
                100                 105                 110
Leu Leu Lys Asp Leu Glu Glu Arg Ile Gln Thr Leu Met Gly Arg Leu
            115                 120                 125
Glu Asp Gly Ser Pro Arg Thr Gly Gln Ile Phe Lys Gln Thr Tyr Ser
130                 135                 140
Lys Phe Asp Thr Asn Ser His Asn Asp Asp Ala Leu Leu Lys Asn Tyr
145                 150                 155                 160
Gly Leu Leu Tyr Cys Phe Arg Lys Asp Met Asp Lys Val Glu Thr Phe
                165                 170                 175
Leu Arg Ile Val Gln Cys Arg Ser Val Glu Gly Ser Cys Gly Phe Gly
            180                 185                 190
Gly Arg Gly Gly Gly Ser Gly Gly Gly Ser Gly Gly Gly Gly
        195                 200                 205
Ser Gly Gly Gly Ser Glu Phe Phe Ser Gly Ser Glu Ala Thr Ala
210                 215                 220
Ala Ile Leu Ser Arg Ala Pro Trp Ser Leu Gln Ser Val Asn Pro Gly
225                 230                 235                 240
Leu Lys Thr Asn Ser Ser Lys Glu Pro Lys Phe Thr Lys Cys Arg Ser
                245                 250                 255
Pro Glu Arg Glu Thr Phe Ser Cys His Trp Thr Asp Glu Val His His
            260                 265                 270
Gly Thr Lys Asn Leu Gly Pro Ile Gln Leu Phe Tyr Thr Arg Arg Asn
275                 280                 285
Thr Gln Glu Trp Thr Gln Glu Trp Lys Glu Cys Pro Asp Tyr Val Ser
290                 295                 300
Ala Gly Glu Asn Ser Cys Tyr Phe Asn Ser Ser Phe Thr Ser Ile Trp
305                 310                 315                 320
Ile Pro Tyr Cys Ile Lys Leu Thr Ser Asn Gly Gly Thr Val Asp Glu
                325                 330                 335
Lys Cys Phe Ser Val Asp Glu Ile Val Gln Pro Asp Pro Pro Ile Ala
            340                 345                 350
Leu Asn Trp Thr Leu Leu Asn Val Ser Leu Thr Gly Ile His Ala Asp
                355                 360                 365
Ile Gln Val Arg Trp Glu Ala Pro Arg Asn Ala Asp Ile Gln Lys Gly
370                 375                 380
Trp Met Val Leu Glu Tyr Glu Leu Gln Tyr Lys Glu Val Asn Glu Thr
385                 390                 395                 400
Lys Trp Lys Met Met Asp Pro Ile Leu Thr Thr Ser Val Pro Val Tyr
                405                 410                 415
Ser Leu Lys Val Asp Lys Glu Tyr Glu Val Arg Val Arg Ser Lys Gln
            420                 425                 430
Arg Asn Ser Gly Asn Tyr Gly Glu Phe Ser Glu Val Leu Tyr Val Thr
        435                 440                 445
Leu Pro Gln Met Ser Gln
        450
```

<210> SEQ ID NO 7
<211> LENGTH: 1440
<212> TYPE: DNA
<213> ORGANISM: Artificial
<220> FEATURE:
<223> OTHER INFORMATION: growth hormone fusion protein

<400> SEQUENCE: 7

| | |
|---|---|
| atggctacag gctcccggac gtccctgctc ctggcttttg gcctgctctg cctgccctgg | 60 |
| cttcaagagg gcagtgcctt cccaaccatt cccttatcca ggcttttga caacgctatg | 120 |
| ctccgcgccc atcgtctgca ccagctggcc tttgacacct accaggagtt tgaagaagcc | 180 |
| tatatcccaa aggaacagaa gtattcattc ctgcagaacc cccagacctc cctctgtttc | 240 |
| tcagagtcta ttccgacacc ctccaacagg gaggaaacac aacagaaatc caacctagag | 300 |
| ctgctccgca tctccctgct gctcatccag tcgtggctgg agcccgtgca gttcctcagg | 360 |
| agtgtcttcg ccaacagcct ggtgtacggc gcctctgaca gcaacgtcta tgacctccta | 420 |
| aaggacctag aggaacgcat ccaaacgctg atggggaggc tggaagatgg cagcccccgg | 480 |
| actgggcaga tcttcaagca gacctacagc aagttcgaca caaactcaca caacgatgac | 540 |
| gcactactca gaactacgg gctgctctac tgcttcagga aggacatgga caaggtcgag | 600 |
| acattcctgc gcatcgtgca gtgccgctct gtggagggcg ctgtggcttc ggtggcgga | 660 |
| ggtagtggtg gcggaggtag cggtggcgga ggttctggtg gcggaggttc cggtggcgga | 720 |
| ggtagttttt ctggaagtga ggccacagca gctatcctta gcagagcacc ctggagtctg | 780 |
| caaagtgtta atccaggcct aaagacaaat tcttctaagg agcctaaatt caccaagtgc | 840 |
| cgttcacctg agcgagagac ttttcatgc cactggacag atgaggttca tcatggtaca | 900 |
| aagaacctag acccataca gctgttctat accagaagga acactcaaga atggactcaa | 960 |
| gaatggaaag aatgccctga ttatgtttct gctggggaaa acagctgtta ctttaattca | 1020 |
| tcgtttacct ccatctggat accttattgt atcaagctaa ctagcaatgg tggtacagtg | 1080 |
| gatgaaaagt gttctctgt tgatgaaata gtgcaaccag atccacccat gccctcaac | 1140 |
| tggactttac tgaacgtcag tttaactggg attcatgcag atatccaagt gagatgggaa | 1200 |
| gcaccacgca atgcagatat tcagaaagga tggatggttc tggagtatga acttcaatac | 1260 |
| aaagaagtaa atgaaactaa atggaaaatg atggacccta tattgacaac atcagttcca | 1320 |
| gtgtactcat tgaaagtgga taggaatat gaagtgcgtg tgagatccaa acaacgaaac | 1380 |
| tctggaaatt atggcgagtt cagtgaggtg ctctatgtaa cacttcctca gatgagccaa | 1440 |

<210> SEQ ID NO 8
<211> LENGTH: 1362
<212> TYPE: DNA
<213> ORGANISM: Artificial
<220> FEATURE:
<223> OTHER INFORMATION: growth hormone fusion protein

<400> SEQUENCE: 8

| | |
|---|---|
| ttcccaacca ttcccttatc caggcttttt gacaacgcta tgctccgcgc ccatcgtctg | 60 |
| caccagctgg cctttgacac ctaccaggag tttgaagaag cctatatccc aaaggaacag | 120 |
| aagtattcat tcctgcagaa cccccagacc tccctctgtt tctcagagtc tattccgaca | 180 |
| ccctccaaca gggaggaaac acaacagaaa tccaacctag agctgctccg catctccctg | 240 |
| ctgctcatcc agtcgtggct ggagcccgtg cagttcctca ggagtgtctt cgccaacagc | 300 |
| ctggtgtacg gcgcctctga cagcaacgtc tatgacctcc taaaggacct agaggaacgc | 360 |

```
atccaaacgc tgatggggag gctggaagat ggcagccccc ggactgggca gatcttcaag      420
cagacctaca gcaagttcga cacaaactca cacaacgatg acgcactact caagaactac      480
gggctgctct actgcttcag gaaggacatg gacaaggtcg agacattcct gcgcatcgtg      540
cagtgccgct ctgtggaggg cagctgtggc ttcggtggcg gaggtagtgg tggcggaggt      600
agcggtggcg gaggttctgg tggcggaggt tccggtggcg gaggtagttt ttctggaagt      660
gaggccacag cagctatcct tagcagagca ccctggagtc tgcaaagtgt taatccaggc      720
ctaaagacaa attcttctaa ggagcctaaa ttcaccaagt gccgttcacc tgagcgagag      780 acttttttcat gccactggac agatgaggtt catcatggta caaagaacct aggacccata      840
cagctgttct ataccagaag gaacactcaa gaatggactc aagaatggaa agaatgccct      900
gattatgttt ctgctgggga aaacagctgt tactttaatt catcgtttac ctccatctgg      960 atacccttatt gtatcaagct aactagcaat ggtggtacag tggatgaaaa gtgtttctct     1020
gttgatgaaa tagtgcaacc agatccaccc attgccctca actggacttt actgaacgtc     1080
agtttaactg ggattcatgc agatatccaa gtgagatggg aagcaccacg caatgcagat     1140
attcagaaag gatggatggt tctggagtat gaacttcaat acaaagaagt aaatgaaact     1200
aaatggaaaa tgatggaccc tatattgaca acatcagttc cagtgtactc attgaaagtg     1260
gataaggaat atgaagtgcg tgtgagatcc aaacaacgaa actctggaaa ttatggcgag     1320
ttcagtgagg tgctctatgt aacacttcct cagatgagcc aa                        1362
```

<210> SEQ ID NO 9  
<211> LENGTH: 454  
<212> TYPE: PRT  
<213> ORGANISM: Artificial  
<220> FEATURE:  
<223> OTHER INFORMATION: growth hormone fusion protein
<400> SEQUENCE: 9

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Arg Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Gly
            180                 185                 190
```

```
Gly Gly Gly Ser Gly Gly Gly Ser Gly Gly Gly Ser Gly Gly
        195                 200                 205
Gly Gly Ser Gly Gly Gly Ser Phe Ser Gly Ser Glu Ala Thr Ala
210                 215                 220
Ala Ile Leu Ser Arg Ala Pro Trp Ser Leu Gln Ser Val Asn Pro Gly
225                 230                 235                 240
Leu Lys Thr Asn Ser Ser Lys Glu Pro Lys Phe Thr Lys Cys Arg Ser
                245                 250                 255
Pro Glu Arg Glu Thr Phe Ser Cys His Trp Thr Asp Glu Val His His
            260                 265                 270
Gly Thr Lys Asn Leu Gly Pro Ile Gln Leu Phe Tyr Thr Arg Arg Asn
        275                 280                 285
Thr Gln Glu Trp Thr Gln Glu Trp Lys Glu Cys Pro Asp Tyr Val Ser
        290                 295                 300
Ala Gly Glu Asn Ser Cys Tyr Phe Asn Ser Ser Phe Thr Ser Ile Trp
305                 310                 315                 320
Ile Pro Tyr Cys Ile Lys Leu Thr Ser Asn Gly Gly Thr Val Asp Glu
                325                 330                 335
Lys Cys Phe Ser Val Asp Glu Ile Val Gln Pro Asp Pro Pro Ile Ala
            340                 345                 350
Leu Asn Trp Thr Leu Leu Asn Val Ser Leu Thr Gly Ile His Ala Asp
        355                 360                 365
Ile Gln Val Arg Trp Glu Ala Pro Arg Asn Ala Asp Ile Gln Lys Gly
    370                 375                 380
Trp Met Val Leu Glu Tyr Glu Leu Gln Tyr Lys Glu Val Asn Glu Thr
385                 390                 395                 400
Lys Trp Lys Met Met Asp Pro Ile Leu Thr Thr Ser Val Pro Val Tyr
                405                 410                 415
Ser Leu Lys Val Asp Lys Glu Tyr Glu Val Arg Val Arg Ser Lys Gln
            420                 425                 430
Arg Asn Ser Gly Asn Tyr Gly Glu Phe Ser Glu Val Leu Tyr Val Thr
        435                 440                 445
Leu Pro Gln Met Ser Gln
    450

<210> SEQ ID NO 10
<211> LENGTH: 1365
<212> TYPE: DNA
<213> ORGANISM: Artificial
<220> FEATURE:
<223> OTHER INFORMATION: growth hormone fusion protein

<400> SEQUENCE: 10
atggctacag gctcccggac gtccctgctc ctggcttttg gcctgctctg cctgccctgg      60
cttcaagagg gcagtgcctt cccaaccatt cccttatcca ggcttttga caacgctatg     120 ctccgcgccc atcgtctgca ccagctggcc tttgacacct accaggagtt tgaagaagcc     180
tatatcccaa aggaacagaa gtattcattc ctgcagaacc cccagacctc cctctgtttc     240
tcagagtcta ttccgacacc ctccaacagg gaggaaacac aacagaaatc caacctagag     300
ctgctccgca tctccctgct gctcatccag tcgtggctgg agcccgtgca gttcctcagg     360
agtgtcttcg ccaacagcct ggtgtacggc gcctctgaca gcaacgtcta tgacctccta     420
aaggacctag aggaacgcat ccaaacgctg atggggaggc tggaagatgg cagccccgg     480 actgggcaga tcttcaagca gacctacagc aagttcgaca caaactcaca caacgatgac     540
```

| | |
|---|---|
| gcactactca agaactacgg gctgctctac tgcttcagga aggacatgga caaggtcgag | 600 |
| acattcctgc gcatcgtgca gtgccgctct gtggagggca gctgtggctt ctttctgga | 660 |
| agtgaggcca cagcagctat ccttagcaga gcaccctgga gtctgcaaag tgttaatcca | 720 |
| ggcctaaaga caaattcttc taaggagcct aaattcacca agtgccgttc acctgagcga | 780 |
| gagactttt catgccactg gacagatgag gttcatcatg gtacaaagaa cctaggaccc | 840 |
| atacagctgt tctataccag aaggaacact caagaatgga ctcaagaatg gaagaatgc | 900 |
| cctgattatg tttctgctgg ggaaaacagc tgttacttta attcatcgtt tacctccatc | 960 |
| tggataccct attgtatcaa gctaactagc aatggtggta cagtggatga aaagtgtttc | 1020 |
| tctgttgatg aaatagtgca accagatcca cccattgccc tcaactggac tttactgaac | 1080 |
| gtcagtttaa ctgggattca tgcagatatc caagtgagat gggaagcacc acgcaatgca | 1140 |
| gatattcaga aggatggat ggttctggag tatgaacttc aatacaaaga gtaaatgaa | 1200 |
| actaaatgga aaatgatgga ccctatattg acaacatcag ttccagtgta ctcattgaaa | 1260 |
| gtggataagg aatatgaagt gcgtgtgaga tccaaacaac gaaactctgg aaattatggc | 1320 |
| gagttcagtg aggtgctcta tgtaacactt cctcagatga gccaa | 1365 |

```
<210> SEQ ID NO 11
<211> LENGTH: 1287
<212> TYPE: DNA
<213> ORGANISM: Artificial
<220> FEATURE:
<223> OTHER INFORMATION: growth hormone fusion protein

<400> SEQUENCE: 11
```

| | |
|---|---|
| ttcccaacca ttcccttatc caggctttt gacaacgcta tgctccgcgc ccatcgtctg | 60 |
| caccagctgg cctttgacac ctaccaggag tttgaagaag cctatatccc aaaggaacag | 120 |
| aagtattcat tcctgcagaa cccccagacc tccctctgtt tctcagagtc tattccgaca | 180 |
| ccctccaaca gggaggaaac acaacagaaa tccaacctag agctgctccg catctccctg | 240 |
| ctgctcatcc agtcgtggct ggagcccgtg cagttcctca ggagtgtctt cgccaacagc | 300 |
| ctggtgtacg gcgcctctga cagcaacgtc tatgacctcc taaggaccct agaggaacgc | 360 |
| atccaaacgc tgatggggag gctggaagat ggcagccccc ggactgggca gatcttcaag | 420 |
| cagacctaca gcaagttcga cacaaactca cacaacgatg acgcactact caagaactac | 480 |
| gggctgctct actgcttcag gaaggacatg gacaaggtcg agacattcct gcgcatcgtg | 540 |
| cagtgccgct ctgtgagggg cagctgtggc ttcttttctg gaagtgaggc cacagcagct | 600 |
| atccttagca gagcaccctg gagtctgcaa agtgttaatc caggcctaaa gacaaattct | 660 |
| tctaaggagc taaattcac caagtgccgt tcacctgagc gagagacttt tcatgccac | 720 |
| tggacagatg aggttcatca tggtacaaag aacctaggac ccatacagct gttctatacc | 780 |
| agaaggaaca ctcaagaatg gactcaagaa tggaagaat gccctgatta tgtttctgct | 840 |
| ggggaaaaca gctgttactt taattcatcg tttacctcca tctggatacc ttattgtatc | 900 |
| aagctaacta gcaatggtgg tacagtggat gaaaagtgtt tctctgttga tgaaatagtg | 960 |
| caaccagatc cacccattgc cctcaactgg actttactga acgtcagttt aactgggatt | 1020 |
| catgcagata tccaagtgag atgggaagca ccacgcaatg cagatattca gaaggatgg | 1080 |
| atggttctgg agtatgaact tcaatacaaa gaagtaaatg aaactaaatg gaaaatgatg | 1140 |
| gaccctatat tgacaacatc agttccagtg tactcattga agtggataa ggaatatgaa | 1200 |
| gtgcgtgtga gatccaaaca acgaaactct ggaaattatg gcgagttcag tgaggtgctc | 1260 | tatgtaacac ttcctcagat gagccaa         1287

<210> SEQ ID NO 12
<211> LENGTH: 429
<212> TYPE: PRT
<213> ORGANISM: Artificial
<220> FEATURE:
<223> OTHER INFORMATION: growth hormone fusion protein

<400> SEQUENCE: 12

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Arg Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Phe
            180                 185                 190

Ser Gly Ser Glu Ala Thr Ala Ala Ile Leu Ser Arg Ala Pro Trp Ser
        195                 200                 205

Leu Gln Ser Val Asn Pro Gly Leu Lys Thr Asn Ser Ser Lys Glu Pro
    210                 215                 220

Lys Phe Thr Lys Cys Arg Ser Pro Glu Arg Glu Thr Phe Ser Cys His
225                 230                 235                 240

Trp Thr Asp Glu Val His His Gly Thr Lys Asn Leu Gly Pro Ile Gln
                245                 250                 255

Leu Phe Tyr Thr Arg Arg Asn Thr Gln Glu Trp Thr Gln Glu Trp Lys
            260                 265                 270

Glu Cys Pro Asp Tyr Val Ser Ala Gly Glu Asn Ser Cys Tyr Phe Asn
        275                 280                 285

Ser Ser Phe Thr Ser Ile Trp Ile Pro Tyr Cys Ile Lys Leu Thr Ser
    290                 295                 300

Asn Gly Gly Thr Val Asp Glu Lys Cys Phe Ser Val Asp Glu Ile Val
305                 310                 315                 320

Gln Pro Asp Pro Pro Ile Ala Leu Asn Trp Thr Leu Leu Asn Val Ser
                325                 330                 335

Leu Thr Gly Ile His Ala Asp Ile Gln Val Arg Trp Glu Ala Pro Arg
            340                 345                 350

Asn Ala Asp Ile Gln Lys Gly Trp Met Val Leu Glu Tyr Glu Leu Gln
        355                 360                 365
```

```
Tyr Lys Glu Val Asn Glu Thr Lys Trp Lys Met Met Asp Pro Ile Leu
    370                 375                 380

Thr Thr Ser Val Pro Val Tyr Ser Leu Lys Val Asp Lys Glu Tyr Glu
385                 390                 395                 400

Val Arg Val Arg Ser Lys Gln Arg Asn Ser Gly Asn Tyr Gly Glu Phe
                405                 410                 415

Ser Glu Val Leu Tyr Val Thr Leu Pro Gln Met Ser Gln
                420                 425
```

```
<210> SEQ ID NO 13
<211> LENGTH: 1452
<212> TYPE: DNA
<213> ORGANISM: Artificial
<220> FEATURE:
<223> OTHER INFORMATION: growth hormone fusion protein

<400> SEQUENCE: 13
atggctacag gctcccggac gtccctgctc ctggcttttg gcctgctctg cctgccctgg      60
cttcaagagg gcagtgcctt cccaaccatt cccttatcca ggcttttga caacgctatg     120
ctccgcgccg accgtctgaa ccagctggcc tttgacacct accaggagtt tgaagaagcc     180
tatatcccaa aggaacagaa gtattcattc ctgcagaacc cccagacctc cctctgtttc     240
tcagagtcta ttccgacacc ctccaacagg aggaaacac aacagaaatc caacctagag     300
ctgctccgca tctccctgct gctcatccag tcgtggctgg agcccgtgca gttcctcagg     360
agtgtcttcg ccaacagcct ggtgtacggc gcctctgaca gcaacgtcta tgacctccta     420
aaggacctag aggaacgcat ccaaacgctg atggggaggc tggaagatgg cagccccgg      480
actgggcaga tcttcaagca gacctacagc aagttcgaca caaactcaca caacgatgac     540
gcactactca agaactacgg gctgctctac tgcttcaacg ccgacatgtc aagggtctca     600
acattcctgc gcacagtgca gtgccgctct gtgggagcca gctgtggctt cggcggccgc     660
ggtggcggag gtagtggtgg cggaggtagc ggtggcggag gttctggtgg cggaggttcc     720
gaattctttt ctggaagtga ggccacagca gctatcctta gcagagcacc ctggagtctg     780
caaagtgtta atccaggcct aaagacaaat tcttctaagg agcctaaatt caccaagtgc     840
cgttcacctg agcgagagac ttttcatgc cactggacag atgaggttca tcatggtaca     900
aagaacctag acccataca gctgttctat accagaagga cactcaaga atggactcaa     960
gaatggaaag aatgccctga ttatgtttct gctggggaaa acagctgtta ctttaattca    1020
tcgtttacct ccatctggat accttattgt atcaagctaa ctagcaatgg tggtacagtg    1080
gatgaaaagt gtttctctgt tgatgaaata gtgcaaccag atccacccat tgccctcaac    1140
tggacttac tgaacgtcag tttaactggg attcatgcag atatccaagt gagatgggaa    1200
gcaccacgca atgcagatat tcagaaagga tggatggttc tggagtatga acttcaatac    1260
aaagaagtaa atgaaactaa atggaaaatg atggacccta tattgacaac atcagttcca    1320
gtgtactcat tgaaagtgga taaggaatat gaagtacgcg tgagatccaa acaacgaaac    1380
tctggaaatt atggcgagtt cagtgaggtg ctctatgtaa cacttcctca gatgagccaa    1440
aagcttttcg aa                                                       1452
```

```
<210> SEQ ID NO 14
<211> LENGTH: 1374
<212> TYPE: DNA
<213> ORGANISM: Artificial
<220> FEATURE:
<223> OTHER INFORMATION: growth hormone fusion protein
```

<400> SEQUENCE: 14

```
ttcccaacca ttcccttatc caggcttttt gacaacgcta tgctccgcgc cgaccgtctg      60
aaccagctgg cctttgacac ctaccaggag tttgaagaag cctatatccc aaaggaacag     120
aagtattcat tcctgcagaa cccccagacc tccctctgtt tctcagagtc tattccgaca     180
ccctccaaca gggaggaaac acaacagaaa tccaacctag agctgctccg catctccctg     240
ctgctcatcc agtcgtggct ggagcccgtg cagttcctca ggagtgtctt cgccaacagc     300
ctggtgtacg gcgcctctga cagcaacgtc tatgacctcc taaaggacct agaggaacgc     360
atccaaacgc tgatggggag gctggaagat ggcagccccc ggactgggca gatcttcaag     420
cagacctaca gcaagttcga cacaaactca cacaacgatg acgcactact caagaactac     480
gggctgctct actgcttcaa cgccgacatg tcaagggtct caacattcct gcgcacagtg     540
cagtgccgct ctgtggaggg cagctgtggc ttcggcggcc gcggtggcgg aggtagtggt     600
ggcggaggta gcggtggcgg aggttctggt ggcggaggtt ccgaattctt ttctggaagt     660
gaggccacag cagctatcct tagcagagca ccctggagtc tgcaaagtgt taatccaggc     720
ctaaagacaa attcttctaa ggagcctaaa ttcaccaagt gccgttcacc tgagcgagag     780
acttttttcat gccactggac agatgaggtt catcatggta caaagaaccct aggacccata     840
cagctgttct ataccagaag gaacactcaa gaatggactc aagaatggaa agaatgccct     900
gattatgttt ctgctgggga aacagctgt tactttaatt catcgtttac ctccatctgg     960
atacctattt gtatcaagct aactagcaat ggtggtacag tggatgaaaa gtgtttctct    1020
gttgatgaaa tagtgcaacc agatccaccc attgccctca actggacttt actgaacgtc    1080
agtttaactg ggattcatgc agatatccaa gtgagatggg aagcaccacg caatgcagat    1140
attcagaaag gatggatggt tctggagtat gaacttcaat acaaagaagt aaatgaaact    1200
aaatggaaaa tgatggaccc tatattgaca acatcagttc cagtgtactc attgaaagtg    1260
gataaggaat atgaagtacg cgtgagatcc aaacaacgaa actctggaaa ttatggcgag    1320
ttcagtgagg tgctctatgt aacacttcct cagatgagcc aaaagctttt cgaa           1374
```

<210> SEQ ID NO 15
<211> LENGTH: 458
<212> TYPE: PRT
<213> ORGANISM: Artificial
<220> FEATURE:
<223> OTHER INFORMATION: growth hormone fusion protein

<400> SEQUENCE: 15

```
Phe Pro Thr Ile Pro Leu Ser Arg Leu Phe Asp Asn Ala Met Leu Arg
1               5                   10                  15

Ala Asp Arg Leu Asn Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110
```

Leu Leu Lys Asp Leu Glu Glu Arg Ile Gln Thr Leu Met Gly Arg Leu
    115                 120                 125

Glu Asp Gly Ser Pro Arg Thr Gly Gln Ile Phe Lys Gln Thr Tyr Ser
130                 135                 140

Lys Phe Asp Thr Asn Ser His Asn Asp Asp Ala Leu Leu Lys Asn Tyr
145                 150                 155                 160

Gly Leu Leu Tyr Cys Phe Asn Ala Asp Met Ser Arg Val Ser Thr Phe
                165                 170                 175

Leu Arg Thr Val Gln Cys Arg Ser Val Glu Gly Ser Cys Gly Phe Gly
                180                 185                 190

Gly Arg Gly Gly Gly Ser Gly Gly Gly Ser Gly Gly Gly
            195                 200                 205

Ser Gly Gly Gly Ser Glu Phe Phe Ser Ser Glu Ala Thr Ala
    210                 215                 220

Ala Ile Leu Ser Arg Ala Pro Trp Ser Leu Gln Ser Val Asn Pro Gly
225                 230                 235                 240

Leu Lys Thr Asn Ser Ser Lys Glu Pro Lys Phe Thr Lys Cys Arg Ser
                245                 250                 255

Pro Glu Arg Glu Thr Phe Ser Cys His Trp Thr Asp Glu Val His His
            260                 265                 270

Gly Thr Lys Asn Leu Gly Pro Ile Gln Leu Phe Tyr Thr Arg Arg Asn
            275                 280                 285

Thr Gln Glu Trp Thr Gln Glu Trp Lys Glu Cys Pro Asp Tyr Val Ser
    290                 295                 300

Ala Gly Glu Asn Ser Cys Tyr Phe Asn Ser Ser Phe Thr Ser Ile Trp
305                 310                 315                 320

Ile Pro Tyr Cys Ile Lys Leu Thr Ser Asn Gly Gly Thr Val Asp Glu
                325                 330                 335

Lys Cys Phe Ser Val Asp Glu Ile Val Gln Pro Asp Pro Ile Ala
                340                 345                 350

Leu Asn Trp Thr Leu Leu Asn Val Ser Leu Thr Gly Ile His Ala Asp
            355                 360                 365

Ile Gln Val Arg Trp Glu Ala Pro Arg Asn Ala Asp Ile Gln Lys Gly
    370                 375                 380

Trp Met Val Leu Glu Tyr Glu Leu Gln Tyr Lys Glu Val Asn Glu Thr
385                 390                 395                 400

Lys Trp Lys Met Met Asp Pro Ile Leu Thr Thr Ser Val Pro Val Tyr
                405                 410                 415

Ser Leu Lys Val Asp Lys Glu Tyr Glu Val Arg Val Arg Ser Lys Gln
                420                 425                 430

Arg Asn Ser Gly Asn Tyr Gly Glu Phe Ser Glu Val Leu Tyr Val Thr
            435                 440                 445

Leu Pro Gln Met Ser Gln Lys Leu Phe Glu
    450                 455

<210> SEQ ID NO 16
<211> LENGTH: 1440
<212> TYPE: DNA
<213> ORGANISM: Artificial
<220> FEATURE:
<223> OTHER INFORMATION: growth hormone fusion protein

<400> SEQUENCE: 16
atggctacag gctcccggac gtccctgctc ctggcttttg gcctgctctg cctgccctgg     60
cttcaagagg gcagtgcctt cccaaccatt cccttatcca ggcttttga caacgctatg    120

```
ctccgcgccg accgtctgaa ccagctggcc tttgacacct accaggagtt tgaagaagcc      180
tatatcccaa aggaacagaa gtattcattc ctgcagaacc cccagacctc cctctgtttc      240
tcagagtcta ttccgacacc ctccaacagg aggaaacac aacagaaatc caacctagag       300
ctgctccgca tctccctgct gctcatccag tcgtggctgg agcccgtgca gttcctcagg      360
agtgtcttcg ccaacagcct ggtgtacggc gcctctgaca gcaacgtcta tgacctccta      420
aaggacctag aggaacgcat ccaaacgctg atggggaggc tggaagatgg cagccccgg       480 actgggcaga tcttcaagca gacctacagc aagttcgaca caaactcaca caacgatgac      540
gcactactca agaactacgg gctgctctac tgcttcaacg ccgacatgtc aagggtctca      600
acattcctgc gcacagtgca gtgccgctct gtggagggca gctgtggctt cggcggccgc      660
ggtggcggag gtagtggtgg cggaggtagc ggtggcggag gttctggtgg cggaggttcc      720
gaattctttt ctggaagtga ggccacagca gctatcctta gcagagcacc ctggagtctg      780
caaagtgtta atccaggcct aaagacaaat tcttctaagg agcctaaatt caccaagtgc      840
cgttcacctg agcgagagac ttttttcatgc cactggacag atgaggttca tcatggtaca      900
aagaacctag acccataca gctgttctat accagaagga acactcaaga atggactcaa       960
gaatggaaag aatgccctga ttatgtttct gctggggaaa acagctgtta ctttaattca     1020
tcgtttacct ccatctggat accttattgt atcaagctaa ctagcaatgg tggtacagtg     1080
gatgaaaagt gtttctctgt tgatgaaata gtgcaaccag atccacccat tgccctcaac     1140
tggactttac tgaacgtcag tttaactggg attcatgcag atatccaagt gagatgggaa     1200
gcaccacgca atgcagatat tcagaaagga tggatggttc tggagtatga acttcaatac     1260
aaagaagtaa atgaaactaa atggaaaatg atggaccta tattgacaac atcagttcca      1320
gtgtactcat tgaaagtgga taaggaatat gaagtgcgtg tgagatccaa acaacgaaac     1380
tctggaaatt atggcgagtt cagtgaggtg ctctatgtaa cacttcctca gatgagccaa     1440
```

<210> SEQ ID NO 17
<211> LENGTH: 1362
<212> TYPE: DNA
<213> ORGANISM: Artificial
<220> FEATURE:
<223> OTHER INFORMATION: growth hormone fusion protein

<400> SEQUENCE: 17

```
ttcccaacca ttcccttatc caggcttttt gacaacgcta tgctccgcgc cgaccgtctg       60
aaccagctgg cctttgacac ctaccaggag tttgaagaag cctatatccc aaaggaacag      120
aagtattcat tcctgcagaa cccccagacc tccctctgtt tctcagagtc tattccgaca      180
ccctccaaca gggaggaaac acaacagaaa tccaacctag agctgctccg catctccctg      240
ctgctcatcc agtcgtggct ggagcccgtg cagttcctca ggagtgtctt cgccaacagc      300
ctggtgtacg gcgcctctga cagcaacgtc tatgacctcc taaaggacct agaggaacgc      360
atccaaacgc tgatggggag gctggaagat ggcagccccc ggactgggca gatcttcaag      420
cagacctaca gcaagttcga cacaaactca cacaacgatg acgcactact caagaactac      480
gggctgctct actgcttcaa cgccgacatg tcaagggtct caacattcct gcgcacagtg      540
cagtgccgct ctgtgggggg cagctgtggc ttcggcggcc gcggtggcgg aggtagtggt      600
ggcggaggta gcggtggcgg aggttctggt ggcggaggtt ccgaattctt ttctggaagt      660
gaggccacag cagctatcct tagcagagca ccctggagtc tgcaaagtgt taatccaggc      720
ctaaagacaa attcttctaa ggagcctaaa ttcaccaagt gccgttcacc tgagcgagag      780
```

```
actttttcat gccactggac agatgaggtt catcatggta caaagaacct aggacccata    840
cagctgttct ataccagaag gaacactcaa gaatggactc aagaatggaa agaatgccct    900
gattatgttt ctgctgggga aaacagctgt tactttaatt catcgtttac ctccatctgg    960 atccttatt gtatcaagct aactagcaat ggtggtacag tggatgaaaa gtgtttctct   1020
gttgatgaaa tagtgcaacc agatccaccc attgccctca actggacttt actgaacgtc   1080
agtttaactg ggattcatgc agatatccaa gtgagatggg aagcaccacg caatgcagat   1140
attcagaaag gatggatggt tctggagtat gaacttcaat acaaagaagt aaatgaaact   1200
aaatggaaaa tgatggaccc tatattgaca acatcagttc cagtgtactc attgaaagtg   1260
gataaggaat atgaagtgcg tgtgagatcc aaacaacgaa actctggaaa ttatggcgag   1320
ttcagtgagg tgctctatgt aacacttcct cagatgagcc aa                      1362
```

<210> SEQ ID NO 18
<211> LENGTH: 454
<212> TYPE: PRT
<213> ORGANISM: Artificial
<220> FEATURE:
<223> OTHER INFORMATION: growth hormone fusion protein

<400> SEQUENCE: 18

```
Phe Pro Thr Ile Pro Leu Ser Arg Leu Phe Asp Asn Ala Met Leu Arg
1               5                   10                  15

Ala Asp Arg Leu Asn Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
        50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Arg Ile Gln Thr Leu Met Gly Arg Leu
        115                 120                 125

Glu Asp Gly Ser Pro Arg Thr Gly Gln Ile Phe Lys Gln Thr Tyr Ser
130                 135                 140

Lys Phe Asp Thr Asn Ser His Asn Asp Asp Ala Leu Leu Lys Asn Tyr
145                 150                 155                 160

Gly Leu Leu Tyr Cys Phe Asn Ala Asp Met Ser Arg Val Ser Thr Phe
                165                 170                 175

Leu Arg Thr Val Gln Cys Arg Ser Val Glu Gly Ser Cys Gly Phe Gly
            180                 185                 190

Gly Arg Gly Gly Gly Ser Gly Gly Gly Ser Gly Gly Gly Gly
        195                 200                 205

Ser Gly Gly Gly Ser Glu Phe Phe Ser Gly Ser Glu Ala Thr Ala
    210                 215                 220

Ala Ile Leu Ser Arg Ala Pro Trp Ser Leu Gln Ser Val Asn Pro Gly
225                 230                 235                 240

Leu Lys Thr Asn Ser Ser Lys Glu Pro Lys Phe Thr Lys Cys Arg Ser
                245                 250                 255

Pro Glu Arg Glu Thr Phe Ser Cys His Trp Thr Asp Glu Val His His
            260                 265                 270
```

```
Gly Thr Lys Asn Leu Gly Pro Ile Gln Leu Phe Tyr Thr Arg Arg Asn
            275                 280                 285
Thr Gln Glu Trp Thr Gln Glu Trp Lys Glu Cys Pro Asp Tyr Val Ser
        290                 295                 300
Ala Gly Glu Asn Ser Cys Tyr Phe Asn Ser Phe Thr Ser Ile Trp
305                 310                 315                 320
Ile Pro Tyr Cys Ile Lys Leu Thr Ser Asn Gly Gly Thr Val Asp Glu
                325                 330                 335
Lys Cys Phe Ser Val Asp Glu Ile Val Gln Pro Asp Pro Pro Ile Ala
            340                 345                 350
Leu Asn Trp Thr Leu Leu Asn Val Ser Leu Thr Gly Ile His Ala Asp
        355                 360                 365
Ile Gln Val Arg Trp Glu Ala Pro Arg Asn Ala Asp Ile Gln Lys Gly
370                 375                 380
Trp Met Val Leu Glu Tyr Glu Leu Gln Tyr Lys Glu Val Asn Glu Thr
385                 390                 395                 400
Lys Trp Lys Met Met Asp Pro Ile Leu Thr Thr Ser Val Pro Val Tyr
                405                 410                 415
Ser Leu Lys Val Asp Lys Glu Tyr Glu Val Arg Val Arg Ser Lys Gln
            420                 425                 430
Arg Asn Ser Gly Asn Tyr Gly Glu Phe Ser Glu Val Leu Tyr Val Thr
        435                 440                 445
Leu Pro Gln Met Ser Gln
    450

<210> SEQ ID NO 19
<211> LENGTH: 1440
<212> TYPE: DNA
<213> ORGANISM: Artificial
<220> FEATURE:
<223> OTHER INFORMATION: growth hormone fusion protein

<400> SEQUENCE: 19
atggctacag ctcccggac gtccctgctc ctggcttttg gcctgctctg cctgccctgg      60
cttcaagagg gcagtgcctt cccaaccatt cccttatcca ggcttttga caacgctatg     120 ctccgcgccg accgtctgaa ccagctggcc tttgacacct accaggagtt tgaagaagcc     180
tatatcccaa aggaacagaa gtattcattc ctgcagaacc cccagacctc cctctgtttc     240
tcagagtcta ttccgacacc ctccaacagg gaggaaacac aacagaaatc aacctagag     300 ctgctccgca tctccctgct gctcatccag tcgtggctgg agcccgtgca gttcctcagg     360
agtgtcttcg ccaacagcct ggtgtacggc gcctctgaca gcaacgtcta tgacctccta     420
aaggacctag aggaacgcat ccaaacgctg atggggaggc tggaagatgg cagccccgg     480 actgggcaga tcttcaagca gacctacagc aagttcgaca caaactcaca caacgatgac     540
gcactactca gaactacgg gctgctctac tgcttcaacg ccgacatgtc aagggtctca     600
acattcctgc gcacagtgca gtgccgctct gtgagggca gctgtggctt cggtggcgga     660
ggtagtggtg gcggaggtag cggtggcgga ggttctggtg gcgaggttc cggtggcgga     720 ggtagttttt ctggaagtga ggccacagca gctatcctta gcagagcacc ctggagtctg     780
caaagtgtta tccaggcct aaagacaaat tcttctaagg agcctaaatt caccaagtgc     840
cgttcacctg agcgagagac ttttcatgc cactggacag atgaggttca tcatggtaca     900
aagaacctag acccataca gctgttctat accagaagga cactcaaga atggactcaa     960 gaatggaaag aatgccctga ttatgttttct gctggggaaa acagctgtta ctttaattca    1020
```

```
tcgtttacct ccatctggat accttattgt atcaagctaa ctagcaatgg tggtacagtg   1080
gatgaaaagt gtttctctgt tgatgaaata gtgcaaccag atccaccat tgccctcaac    1140 tggactttac tgaacgtcag tttaactggg attcatgcag atatccaagt gagatgggaa   1200
gcaccacgca atgcagatat tcagaaagga tggatggttc tggagtatga acttcaatac   1260
aaagaagtaa atgaaactaa atggaaaatg atggaccta tattgacaac atcagttcca    1320
gtgtactcat tgaaagtgga taaggaatat gaagtgcgtg tgagatccaa acaacgaaac   1380
tctggaaatt atggcgagtt cagtgaggtg ctctatgtaa cacttcctca gatgagccaa   1440
```

<210> SEQ ID NO 20
<211> LENGTH: 1362
<212> TYPE: DNA
<213> ORGANISM: Artificial
<220> FEATURE:
<223> OTHER INFORMATION: growth hormone fusion protein

<400> SEQUENCE: 20

```
ttcccaacca ttcccttatc caggcttttt gacaacgcta tgctccgcgc cgaccgtctg     60
aaccagctgg cctttgacac ctaccaggag tttgaagaag cctatatccc aaaggaacag    120
aagtattcat tcctgcagaa ccccagacc tccctctgtt tctcagagtc tattccgaca     180
ccctccaaca gggaggaaac acaacagaaa tccaacctag agctgctccg catctccctg    240
ctgctcatcc agtcgtggct ggagcccgtg cagttcctca ggagtgtctt cgccaacagc    300
ctggtgtacg cgcctctga cagcaacgtc tatgacctcc taaggaccct agaggaacgc     360
atccaaacgc tgatggggag ctggaagat ggcagccccc ggactgggca gatcttcaag     420
cagacctaca gcaagttcga cacaaactca cacaacgatg acgcactact caagaactac    480
gggctgctct actgcttcaa cgccgacatg tcaagggtct caacattcct gcgcacagtg    540
cagtgccgct ctgtgagg cagctgtggc ttcggtggcg gaggtagtgg tggcggaggt     600
agcggtggcg gaggttctgg tggcggaggt tccggtggcg gaggtagttt ttctggaagt    660
gaggccacag cagctatcct tagcagaca ccctggagtc tgcaaagtgt taatccaggc     720
ctaaagacaa attcttctaa ggagcctaaa ttcaccaagt gccgttcacc tgagcgagag    780 acttttcat gccactggac agatgaggtt catcatggta caaagaacct aggacccata    840
cagctgttct ataccagaag gaacactcaa gaatggactc aagaatggaa agaatgccct    900
gattatgttt ctgctgggga aaacagctgt tactttaatt catcgtttac ctccatctgg    960
ataccttatt gtatcaagct aactagcaat ggtggtacag tggatgaaaa gtgtttctct   1020
gttgatgaaa tagtgcaacc agatccaccc attgccctca actggacttt actgaacgtc   1080
agtttaactg ggattcatgc agatatccaa gtgagatggg aagcaccacg caatgcagat   1140
attcagaaag gatggatggt tctggagtat gaacttcaat acaaagaagt aaatgaaact   1200
aaatggaaaa tgatggaccc tatattgaca acatcagttc cagtgtactc attgaaagtg   1260
gataaggaat atgaagtgcg tgtgagatcc aaacaacgaa actctggaaa ttatggcgag   1320
ttcagtgagg tgctctatgt aacacttcct cagatgagcc aa                     1362
```

<210> SEQ ID NO 21
<211> LENGTH: 454
<212> TYPE: PRT
<213> ORGANISM: Artificial
<220> FEATURE:
<223> OTHER INFORMATION: growth hormone fusion protein

<400> SEQUENCE: 21

```
Phe Pro Thr Ile Pro Leu Ser Arg Leu Phe Asp Asn Ala Met Leu Arg
1               5                   10                  15

Ala Asp Arg Leu Asn Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
                35                  40                  45

Gln Thr Ser Leu Cys Phe Ser Glu Ser Ile Pro Thr Pro Ser Asn Arg
50                  55                      60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Glu Glu Arg Ile Gln Thr Leu Met Gly Arg Leu
            115                 120                 125

Glu Asp Gly Ser Pro Arg Thr Gly Gln Ile Phe Lys Gln Thr Tyr Ser
130                 135                 140

Lys Phe Asp Thr Asn Ser His Asn Asp Asp Ala Leu Leu Lys Asn Tyr
145                 150                 155                 160

Gly Leu Leu Tyr Cys Phe Asn Ala Asp Met Ser Arg Val Ser Thr Phe
                165                 170                 175

Leu Arg Thr Val Gln Cys Arg Ser Val Glu Gly Ser Cys Gly Phe Gly
            180                 185                 190

Gly Gly Gly Ser Gly Gly Gly Gly Ser Gly Gly Gly Ser Gly Gly
        195                 200                 205

Gly Gly Ser Gly Gly Gly Ser Phe Ser Gly Ser Glu Ala Thr Ala
210                 215                 220

Ala Ile Leu Ser Arg Ala Pro Trp Ser Leu Gln Ser Val Asn Pro Gly
225                 230                 235                 240

Leu Lys Thr Asn Ser Ser Lys Glu Pro Lys Phe Thr Lys Cys Arg Ser
            245                 250                 255

Pro Glu Arg Glu Thr Phe Ser Cys His Trp Thr Asp Glu Val His His
            260                 265                 270

Gly Thr Lys Asn Leu Gly Pro Ile Gln Leu Phe Tyr Thr Arg Arg Asn
            275                 280                 285

Thr Gln Glu Trp Thr Gln Glu Trp Lys Glu Cys Pro Asp Tyr Val Ser
    290                 295                 300

Ala Gly Glu Asn Ser Cys Tyr Phe Asn Ser Ser Phe Thr Ser Ile Trp
305                 310                 315                 320

Ile Pro Tyr Cys Ile Lys Leu Thr Ser Asn Gly Gly Thr Val Asp Glu
            325                 330                 335

Lys Cys Phe Ser Val Asp Glu Ile Val Gln Pro Asp Pro Pro Ile Ala
            340                 345                 350

Leu Asn Trp Thr Leu Leu Asn Val Ser Leu Thr Gly Ile His Ala Asp
            355                 360                 365

Ile Gln Val Arg Trp Glu Ala Pro Arg Asn Ala Asp Ile Gln Lys Gly
            370                 375                 380

Trp Met Val Leu Glu Tyr Glu Leu Gln Tyr Lys Glu Val Asn Glu Thr
385                 390                 395                 400

Lys Trp Lys Met Met Asp Pro Ile Leu Thr Thr Ser Val Pro Val Tyr
                405                 410                 415

Ser Leu Lys Val Asp Lys Glu Tyr Glu Val Arg Val Arg Ser Lys Gln
```

```
            420              425              430
Arg Asn Ser Gly Asn Tyr Gly Glu Phe Ser Glu Val Leu Tyr Val Thr
        435              440              445

Leu Pro Gln Met Ser Gln
    450
```

<210> SEQ ID NO 22
<211> LENGTH: 1365
<212> TYPE: DNA
<213> ORGANISM: Artificial
<220> FEATURE:
<223> OTHER INFORMATION: growth hormone fusion protein

<400> SEQUENCE: 22

```
atggctacag gctcccggac gtccctgctc ctggcttttg gcctgctctg cctgccctgg      60
cttcaagagg gcagtgcctt cccaaccatt cccttatcca ggcttttga caacgctatg     120
ctccgcgccg accgtctgaa ccagctggcc tttgacacct accaggagtt tgaagaagcc    180
tatatcccaa aggaacagaa gtattcattc ctgcagaacc cccagacctc cctctgtttc    240
tcagagtcta ttccgacacc ctccaacagg aggaaacac aacagaaatc caacctagag     300
ctgctccgca tctccctgct gctcatccag tcgtggctgg agcccgtgca gttcctcagg    360
agtgtcttcg ccaacagcct ggtgtacggc cctctgaca gcaacgtcta tgacctccta    420
aaggacctag aggaacgcat ccaaacgctg atggggaggc tggaagatgg cagccccgg    480
actgggcaga tcttcaagca gacctacagc aagttcgaca caactcaca caacgatgac   540
gcactactca agaactacgg gctgctctac tgcttcaacg ccgacatgtc aagggtctca   600
acattcctgc gcacagtgca gtgccgctct gtggagggca gctgtggctt ctttctgga    660
agtgaggcca cagcagctat ccttagcaga gcaccctgga gtctgcaaag tgttaatcca    720
ggcctaaaga caaattcttc taaggagcct aaattcacca gtgccgttca acctgagcga    780
gagacttttt catgccactg gacagatgag gttcatcatg gtacaaagaa cctaggaccc    840
atacagctgt tctataccag aaggaacact caagaatgga ctcaagaatg gaaagaatgc    900
cctgattatg tttctgctgg ggaaaacagc tgttacttta ttcatcgtt acctccatc    960
tggatacctt attgtatcaa gctaactagc aatggtggta cagtggatga aaagtgtttc    1020
tctgttgatg aaatagtgca accagatcca cccattgccc tcaactggac tttactgaac    1080
gtcagtttaa ctgggattca tgcagatatc caagtgagat gggaagcacc acgcaatgca    1140
gatattcaga aaggatggat ggttctggag tatgaacttc aatacaaaga agtaaatgaa    1200
actaaatgga aaatgatgga ccctatattg acaacatcag ttccagtgta ctcattgaaa    1260
gtggataagg aatatgaagt gcgtgtgaga tccaaacaac gaaactctgg aaattatggc    1320
gagttcagtg aggtgctcta tgtaacactt cctcagatga gccaa                   1365
```

<210> SEQ ID NO 23
<211> LENGTH: 1287
<212> TYPE: DNA
<213> ORGANISM: Artificial
<220> FEATURE:
<223> OTHER INFORMATION: growth hormone fusion protein

<400> SEQUENCE: 23

```
ttcccaacca ttcccttatc caggcttttt gacaacgcta tgctccgcgc cgaccgtctg     60
aaccagctgg cctttgacac ctaccaggag tttgaagaag cctatatccc aaaggaacag   120
aagtattcat tcctgcagaa cccccagacc tccctctgtt tctcagagtc tattccgaca    180
```

-continued

```
ccctccaaca gggaggaaac acaacagaaa tccaacctag agctgctccg catctccctg    240
ctgctcatcc agtcgtggct ggagcccgtg cagttcctca ggagtgtctt cgccaacagc    300
ctggtgtacg gcgcctctga cagcaacgtc tatgacctcc taaaggacct agaggaacgc    360
atccaaacgc tgatggggag gctggaagat ggcagccccc ggactgggca gatcttcaag    420
cagacctaca gcaagttcga cacaaactca caacgatg acgcactact caagaactac      480
gggctgctct actgcttcaa cgccgacatg tcaagggtct caacattcct cgcacagtg    540 cagtgccgct ctgtggaggg cagctgtggc ttcttttctg gaagtgaggc cacagcagct    600
atccttagca gagcaccctg gagtctgcaa agtgttaatc aggcctaaa gacaaattct     660 tctaaggagc ctaaattcac caagtgccgt tcacctgagc gagagacttt ttcatgccac    720
tggacagatg aggttcatca tggtacaaag aacctaggac ccatacagct gttctatacc    780
agaaggaaca ctcaagaatg gactcaagaa tggaaagaat gccctgatta tgtttctgct    840
ggggaaaaca gctgttactt taattcatcg tttacctcca tctggatacc ttattgtatc    900
aagctaacta gcaatggtgg tacagtggat gaaaagtgtt tctctgttga tgaaatagtg    960
caaccagatc cacccattgc cctcaactgg actttactga acgtcagttt aactgggatt   1020
catgcagata tccaagtgag atgggaagca ccacgcaatg cagatattca gaaaggatgg   1080
atggttctgg agtatgaact tcaatacaaa gaagtaaatg aaactaaatg gaaaatgatg   1140
gaccctatat tgacaacatc agttccagtg tactcattga aagtggataa ggaatatgaa   1200
gtgcgtgtga gatccaaaca acgaaactct ggaaattatg gcgagttcag tgaggtgctc   1260
tatgtaacac ttcctcagat gagccaa                                       1287
```

<210> SEQ ID NO 24
<211> LENGTH: 429
<212> TYPE: PRT
<213> ORGANISM: Artificial
<220> FEATURE:
<223> OTHER INFORMATION: growth hormone fusion protein

<400> SEQUENCE: 24

```
Phe Pro Thr Ile Pro Leu Ser Arg Leu Phe Asp Asn Ala Met Leu Arg
1               5                   10                  15

Ala Asp Arg Leu Asn Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Arg Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Asn Ala Asp Met Ser Arg Val Ser Thr Phe
                165                 170                 175
```

```
Leu Arg Thr Val Gln Cys Arg Ser Val Glu Gly Ser Cys Gly Phe Phe
            180                 185                 190

Ser Gly Ser Glu Ala Thr Ala Ala Ile Leu Ser Arg Ala Pro Trp Ser
        195                 200                 205

Leu Gln Ser Val Asn Pro Gly Leu Lys Thr Asn Ser Ser Lys Glu Pro
    210                 215                 220

Lys Phe Thr Lys Cys Arg Ser Pro Glu Arg Glu Thr Phe Ser Cys His
225                 230                 235                 240

Trp Thr Asp Glu Val His His Gly Thr Lys Asn Leu Gly Pro Ile Gln
                245                 250                 255

Leu Phe Tyr Thr Arg Arg Asn Thr Gln Glu Trp Thr Gln Glu Trp Lys
            260                 265                 270

Glu Cys Pro Asp Tyr Val Ser Ala Gly Glu Asn Ser Cys Tyr Phe Asn
        275                 280                 285

Ser Ser Phe Thr Ser Ile Trp Ile Pro Tyr Cys Ile Lys Leu Thr Ser
    290                 295                 300

Asn Gly Gly Thr Val Asp Glu Lys Cys Phe Ser Val Asp Glu Ile Val
305                 310                 315                 320

Gln Pro Asp Pro Pro Ile Ala Leu Asn Trp Thr Leu Leu Asn Val Ser
                325                 330                 335

Leu Thr Gly Ile His Ala Asp Ile Gln Val Arg Trp Glu Ala Pro Arg
            340                 345                 350

Asn Ala Asp Ile Gln Lys Gly Trp Met Val Leu Glu Tyr Glu Leu Gln
        355                 360                 365

Tyr Lys Glu Val Asn Glu Thr Lys Trp Lys Met Met Asp Pro Ile Leu
    370                 375                 380

Thr Thr Ser Val Pro Val Tyr Ser Leu Lys Val Asp Lys Glu Tyr Glu
385                 390                 395                 400

Val Arg Val Arg Ser Lys Gln Arg Asn Ser Gly Asn Tyr Gly Glu Phe
                405                 410                 415

Ser Glu Val Leu Tyr Val Thr Leu Pro Gln Met Ser Gln
            420                 425

<210> SEQ ID NO 25
<211> LENGTH: 484
<212> TYPE: PRT
<213> ORGANISM: Artificial
<220> FEATURE:
<223> OTHER INFORMATION: growth hormone fusion protein

<400> SEQUENCE: 25

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110
```

```
Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Gly Arg Gly Gly Gly Gly
    210                 215                 220

Ser Gly Gly Gly Gly Ser Gly Gly Gly Ser Gly Gly Gly Gly Ser
225                 230                 235                 240

Glu Phe Phe Ser Gly Ser Glu Ala Thr Ala Ile Leu Ser Arg Ala
                245                 250                 255

Pro Trp Ser Leu Gln Ser Val Asn Pro Gly Leu Lys Thr Asn Ser Ser
        260                 265                 270

Lys Glu Pro Lys Phe Thr Lys Cys Arg Ser Pro Glu Arg Glu Thr Phe
        275                 280                 285

Ser Cys His Trp Thr Asp Glu Val His His Gly Thr Lys Asn Leu Gly
        290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335

Tyr Phe Asn Ser Ser Phe Thr Ser Ile Trp Ile Pro Tyr Cys Ile Lys
            340                 345                 350

Leu Thr Ser Asn Gly Gly Thr Val Asp Glu Lys Cys Phe Ser Val Asp
        355                 360                 365

Glu Ile Val Gln Pro Asp Pro Pro Ile Ala Leu Asn Trp Thr Leu Leu
370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                405                 410                 415

Glu Leu Gln Tyr Lys Glu Val Asn Glu Thr Lys Trp Lys Met Met Asp
            420                 425                 430

Pro Ile Leu Thr Thr Ser Val Pro Val Tyr Ser Leu Lys Val Asp Lys
        435                 440                 445

Glu Tyr Glu Val Arg Val Arg Ser Lys Gln Arg Asn Ser Gly Asn Tyr
    450                 455                 460

Gly Glu Phe Ser Glu Val Leu Tyr Val Thr Leu Pro Gln Met Ser Gln
465                 470                 475                 480

Lys Leu Phe Glu

<210> SEQ ID NO 26
<211> LENGTH: 480
<212> TYPE: PRT
<213> ORGANISM: Artificial
<220> FEATURE:
<223> OTHER INFORMATION: growth hormone fusion protein

<400> SEQUENCE: 26
```

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Gly Arg Gly Gly Gly Gly
    210                 215                 220

Ser Gly Gly Gly Gly Ser Gly Gly Gly Gly Ser Gly Gly Gly Gly Ser
225                 230                 235                 240

Glu Phe Phe Ser Gly Ser Glu Ala Thr Ala Ala Ile Leu Ser Arg Ala
                245                 250                 255

Pro Trp Ser Leu Gln Ser Val Asn Pro Gly Leu Lys Thr Asn Ser Ser
            260                 265                 270

Lys Glu Pro Lys Phe Thr Lys Cys Arg Ser Pro Glu Arg Glu Thr Phe
        275                 280                 285

Ser Cys His Trp Thr Asp Glu Val His His Gly Thr Lys Asn Leu Gly
    290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335

Tyr Phe Asn Ser Ser Phe Thr Ser Ile Trp Ile Pro Tyr Cys Ile Lys
            340                 345                 350

Leu Thr Ser Asn Gly Gly Thr Val Asp Glu Lys Cys Phe Ser Val Asp
        355                 360                 365

Glu Ile Val Gln Pro Asp Pro Pro Ile Ala Leu Asn Trp Thr Leu Leu
    370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                405                 410                 415

Glu Leu Gln Tyr Lys Glu Val Asn Glu Thr Lys Trp Lys Met Met Asp
```

```
                420             425             430
Pro Ile Leu Thr Thr Ser Val Pro Val Tyr Ser Leu Lys Val Asp Lys
            435                 440                 445

Glu Tyr Glu Val Arg Val Arg Ser Lys Gln Arg Asn Ser Gly Asn Tyr
450                 455                 460

Gly Glu Phe Ser Glu Val Leu Tyr Val Thr Leu Pro Gln Met Ser Gln
465                 470                 475                 480

<210> SEQ ID NO 27
<211> LENGTH: 480
<212> TYPE: PRT
<213> ORGANISM: Artificial
<220> FEATURE:
<223> OTHER INFORMATION: growth hormone fusion protein

<400> SEQUENCE: 27

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Gly Gly Ser Gly Gly
    210                 215                 220

Gly Gly Ser Gly Gly Gly Ser Gly Gly Gly Ser Gly Gly Gly
225                 230                 235                 240

Gly Ser Phe Ser Gly Ser Glu Ala Thr Ala Ala Ile Leu Ser Arg Ala
                245                 250                 255

Pro Trp Ser Leu Gln Ser Val Asn Pro Gly Leu Lys Thr Asn Ser Ser
            260                 265                 270

Lys Glu Pro Lys Phe Thr Lys Cys Arg Ser Pro Glu Arg Glu Thr Phe
        275                 280                 285

Ser Cys His Trp Thr Asp Glu Val His His Gly Thr Lys Asn Leu Gly
    290                 295                 300

Pro Ile Gln Leu Phe Tyr Thr Arg Arg Asn Thr Gln Glu Trp Thr Gln
305                 310                 315                 320
```

```
Glu Trp Lys Glu Cys Pro Asp Tyr Val Ser Ala Gly Glu Asn Ser Cys
                325                 330                 335
Tyr Phe Asn Ser Ser Phe Thr Ser Ile Trp Ile Pro Tyr Cys Ile Lys
                340                 345                 350
Leu Thr Ser Asn Gly Gly Thr Val Asp Glu Lys Cys Phe Ser Val Asp
                355                 360                 365
Glu Ile Val Gln Pro Asp Pro Pro Ile Ala Leu Asn Trp Thr Leu Leu
                370                 375                 380
Asn Val Ser Leu Thr Gly Ile His Ala Asp Ile Gln Val Arg Trp Glu
385                 390                 395                 400
Ala Pro Arg Asn Ala Asp Ile Gln Lys Gly Trp Met Val Leu Glu Tyr
                405                 410                 415
Glu Leu Gln Tyr Lys Glu Val Asn Glu Thr Lys Trp Lys Met Met Asp
                420                 425                 430
Pro Ile Leu Thr Thr Ser Val Pro Val Tyr Ser Leu Lys Val Asp Lys
                435                 440                 445
Glu Tyr Glu Val Arg Val Arg Ser Lys Gln Arg Asn Ser Gly Asn Tyr
                450                 455                 460
Gly Glu Phe Ser Glu Val Leu Tyr Val Thr Leu Pro Gln Met Ser Gln
465                 470                 475                 480

<210> SEQ ID NO 28
<211> LENGTH: 455
<212> TYPE: PRT
<213> ORGANISM: Artificial
<220> FEATURE:
<223> OTHER INFORMATION: growth hormone fusion protein

<400> SEQUENCE: 28

Met Ala Thr Gly Ser Arg Thr Ser Leu Leu Leu Ala Phe Gly Leu Leu
1               5                   10                  15
Cys Leu Pro Trp Leu Gln Glu Gly Ser Ala Phe Pro Thr Ile Pro Leu
                20                  25                  30
Ser Arg Leu Phe Asp Asn Ala Met Leu Arg Ala His Arg Leu His Gln
                35                  40                  45
Leu Ala Phe Asp Thr Tyr Gln Glu Phe Glu Glu Ala Tyr Ile Pro Lys
            50                  55                  60
Glu Gln Lys Tyr Ser Phe Leu Gln Asn Pro Gln Thr Ser Leu Cys Phe
65                  70                  75                  80
Ser Glu Ser Ile Pro Thr Pro Ser Asn Arg Glu Glu Thr Gln Gln Lys
                85                  90                  95
Ser Asn Leu Glu Leu Leu Arg Ile Ser Leu Leu Leu Ile Gln Ser Trp
                100                 105                 110
Leu Glu Pro Val Gln Phe Leu Arg Ser Val Phe Ala Asn Ser Leu Val
                115                 120                 125
Tyr Gly Ala Ser Asp Ser Asn Val Tyr Asp Leu Leu Lys Asp Leu Glu
            130                 135                 140
Glu Arg Ile Gln Thr Leu Met Gly Arg Leu Glu Asp Gly Ser Pro Arg
145                 150                 155                 160
Thr Gly Gln Ile Phe Lys Gln Thr Tyr Ser Lys Phe Asp Thr Asn Ser
                165                 170                 175
His Asn Asp Asp Ala Leu Leu Lys Asn Tyr Gly Leu Leu Tyr Cys Phe
                180                 185                 190
Arg Lys Asp Met Asp Lys Val Glu Thr Phe Leu Arg Ile Val Gln Cys
                195                 200                 205
```

```
Arg Ser Val Glu Gly Ser Cys Gly Phe Phe Ser Gly Ser Glu Ala Thr
            210                 215                 220
Ala Ala Ile Leu Ser Arg Ala Pro Trp Ser Leu Gln Ser Val Asn Pro
225                 230                 235                 240
Gly Leu Lys Thr Asn Ser Ser Lys Glu Pro Lys Phe Thr Lys Cys Arg
                    245                 250                 255
Ser Pro Glu Arg Glu Thr Phe Ser Cys His Trp Thr Asp Glu Val His
                260                 265                 270
His Gly Thr Lys Asn Leu Gly Pro Ile Gln Leu Phe Tyr Thr Arg Arg
                275                 280                 285
Asn Thr Gln Glu Trp Thr Gln Glu Trp Lys Glu Cys Pro Asp Tyr Val
            290                 295                 300
Ser Ala Gly Glu Asn Ser Cys Tyr Phe Asn Ser Ser Phe Thr Ser Ile
305                 310                 315                 320
Trp Ile Pro Tyr Cys Ile Lys Leu Thr Ser Asn Gly Gly Thr Val Asp
                    325                 330                 335
Glu Lys Cys Phe Ser Val Asp Glu Ile Val Gln Pro Asp Pro Pro Ile
                340                 345                 350
Ala Leu Asn Trp Thr Leu Leu Asn Val Ser Leu Thr Gly Ile His Ala
                355                 360                 365
Asp Ile Gln Val Arg Trp Glu Ala Pro Arg Asn Ala Asp Ile Gln Lys
            370                 375                 380
Gly Trp Met Val Leu Glu Tyr Glu Leu Gln Tyr Lys Glu Val Asn Glu
385                 390                 395                 400
Thr Lys Trp Lys Met Met Asp Pro Ile Leu Thr Thr Ser Val Pro Val
                    405                 410                 415
Tyr Ser Leu Lys Val Asp Lys Glu Tyr Glu Val Arg Val Arg Ser Lys
                420                 425                 430
Gln Arg Asn Ser Gly Asn Tyr Gly Glu Phe Ser Glu Val Leu Tyr Val
            435                 440                 445
Thr Leu Pro Gln Met Ser Gln
        450                 455

<210> SEQ ID NO 29
<211> LENGTH: 484
<212> TYPE: PRT
<213> ORGANISM: Artificial
<220> FEATURE:
<223> OTHER INFORMATION: growth hormone fusion protein

<400> SEQUENCE: 29

Met Ala Thr Gly Ser Arg Thr Ser Leu Leu Leu Ala Phe Gly Leu Leu
1               5                   10                  15
Cys Leu Pro Trp Leu Gln Glu Gly Ser Ala Phe Pro Thr Ile Pro Leu
                20                  25                  30
Ser Arg Leu Phe Asp Asn Ala Met Leu Arg Ala Asp Arg Leu Asn Gln
            35                  40                  45
Leu Ala Phe Asp Thr Tyr Gln Glu Phe Glu Glu Ala Tyr Ile Pro Lys
50                  55                  60
Glu Gln Lys Tyr Ser Phe Leu Gln Asn Pro Gln Thr Ser Leu Cys Phe
65                  70                  75                  80
Ser Glu Ser Ile Pro Thr Pro Ser Asn Arg Glu Glu Thr Gln Gln Lys
                85                  90                  95
Ser Asn Leu Glu Leu Leu Arg Ile Ser Leu Leu Leu Ile Gln Ser Trp
            100                 105                 110
Leu Glu Pro Val Gln Phe Leu Arg Ser Val Phe Ala Asn Ser Leu Val
```

```
                115                 120                 125
Tyr Gly Ala Ser Asp Ser Asn Val Tyr Asp Leu Leu Lys Asp Leu Glu
            130                 135                 140
Glu Arg Ile Gln Thr Leu Met Gly Arg Leu Glu Asp Gly Ser Pro Arg
145                 150                 155                 160
Thr Gly Gln Ile Phe Lys Gln Thr Tyr Ser Lys Phe Asp Thr Asn Ser
                165                 170                 175
His Asn Asp Asp Ala Leu Leu Lys Asn Tyr Gly Leu Leu Tyr Cys Phe
            180                 185                 190
Asn Ala Asp Met Ser Arg Val Ser Thr Phe Leu Arg Thr Val Gln Cys
                195                 200                 205
Arg Ser Val Glu Gly Ser Cys Gly Phe Gly Gly Arg Gly Gly Gly Gly
            210                 215                 220
Ser Gly Gly Gly Gly Ser Gly Gly Gly Gly Ser Gly Gly Gly Gly Ser
225                 230                 235                 240
Glu Phe Phe Ser Gly Ser Glu Ala Thr Ala Ile Leu Ser Arg Ala
                245                 250                 255
Pro Trp Ser Leu Gln Ser Val Asn Pro Gly Leu Lys Thr Asn Ser Ser
            260                 265                 270
Lys Glu Pro Lys Phe Thr Lys Cys Arg Ser Pro Glu Arg Glu Thr Phe
        275                 280                 285
Ser Cys His Trp Thr Asp Glu Val His His Gly Thr Lys Asn Leu Gly
            290                 295                 300
Pro Ile Gln Leu Phe Tyr Thr Arg Arg Asn Thr Gln Glu Trp Thr Gln
305                 310                 315                 320
Glu Trp Lys Glu Cys Pro Asp Tyr Val Ser Ala Gly Glu Asn Ser Cys
                325                 330                 335
Tyr Phe Asn Ser Ser Phe Thr Ser Ile Trp Ile Pro Tyr Cys Ile Lys
            340                 345                 350
Leu Thr Ser Asn Gly Gly Thr Val Asp Glu Lys Cys Phe Ser Val Asp
        355                 360                 365
Glu Ile Val Gln Pro Asp Pro Pro Ile Ala Leu Asn Trp Thr Leu Leu
    370                 375                 380
Asn Val Ser Leu Thr Gly Ile His Ala Asp Ile Gln Val Arg Trp Glu
385                 390                 395                 400
Ala Pro Arg Asn Ala Asp Ile Gln Lys Gly Trp Met Val Leu Glu Tyr
                405                 410                 415
Glu Leu Gln Tyr Lys Glu Val Asn Glu Thr Lys Trp Lys Met Met Asp
            420                 425                 430
Pro Ile Leu Thr Thr Ser Val Pro Val Tyr Ser Leu Lys Val Asp Lys
        435                 440                 445
Glu Tyr Glu Val Arg Val Arg Ser Lys Gln Arg Asn Ser Gly Asn Tyr
    450                 455                 460
Gly Glu Phe Ser Glu Val Leu Tyr Val Thr Leu Pro Gln Met Ser Gln
465                 470                 475                 480
Lys Leu Phe Glu

<210> SEQ ID NO 30
<211> LENGTH: 480
<212> TYPE: PRT
<213> ORGANISM: Artificial
<220> FEATURE:
<223> OTHER INFORMATION: growth hormone fusion protein

<400> SEQUENCE: 30
```

-continued

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala Asp Arg Leu Asn Gln
            35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Asn Ala Asp Met Ser Arg Val Ser Thr Phe Leu Arg Thr Val Gln Cys
        195                 200                 205

Arg Ser Val Glu Gly Ser Cys Gly Phe Gly Arg Gly Gly Gly Gly Gly
    210                 215                 220

Ser Gly Gly Gly Gly Ser Gly Gly Gly Gly Ser Gly Gly Gly Gly Ser
225                 230                 235                 240

Glu Phe Phe Ser Gly Ser Glu Ala Thr Ala Ala Ile Leu Ser Arg Ala
                245                 250                 255

Pro Trp Ser Leu Gln Ser Val Asn Pro Gly Leu Lys Thr Asn Ser Ser
            260                 265                 270

Lys Glu Pro Lys Phe Thr Lys Cys Arg Ser Pro Glu Arg Glu Thr Phe
        275                 280                 285

Ser Cys His Trp Thr Asp Glu Val His His Gly Thr Lys Asn Leu Gly
    290                 295                 300

Pro Ile Gln Leu Phe Tyr Thr Arg Arg Asn Thr Gln Glu Trp Thr Gln
305                 310                 315                 320

Glu Trp Lys Glu Cys Pro Asp Tyr Val Ser Ala Gly Glu Asn Ser Cys
                325                 330                 335

Tyr Phe Asn Ser Ser Phe Thr Ser Ile Trp Ile Pro Tyr Cys Ile Lys
            340                 345                 350

Leu Thr Ser Asn Gly Gly Thr Val Asp Glu Lys Cys Phe Ser Val Asp
        355                 360                 365

Glu Ile Val Gln Pro Asp Pro Pro Ile Ala Leu Asn Trp Thr Leu Leu
    370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
                405                 410                 415

Glu Leu Gln Tyr Lys Glu Val Asn Glu Thr Lys Trp Lys Met Met Asp
            420                 425                 430
```

```
Pro Ile Leu Thr Thr Ser Val Pro Val Tyr Ser Leu Lys Val Asp Lys
            435                 440                 445

Glu Tyr Glu Val Arg Val Arg Ser Lys Gln Arg Asn Ser Gly Asn Tyr
450                 455                 460

Gly Glu Phe Ser Glu Val Leu Tyr Val Thr Leu Pro Gln Met Ser Gln
465                 470                 475                 480

<210> SEQ ID NO 31
<211> LENGTH: 480
<212> TYPE: PRT
<213> ORGANISM: Artificial
<220> FEATURE:
<223> OTHER INFORMATION: growth hormone fusion protein

<400> SEQUENCE: 31

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala Asp Arg Leu Asn Gln
        35                  40                  45

Leu Ala Phe Asp Thr Tyr Gln Glu Phe Glu Glu Ala Tyr Ile Pro Lys
50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
            85                  90                  95

Ser Asn Leu Glu Leu Leu Arg Ile Ser Leu Leu Leu Ile Gln Ser Trp
        100                 105                 110

Leu Glu Pro Val Gln Phe Leu Arg Ser Val Phe Ala Asn Ser Leu Val
    115                 120                 125

Tyr Gly Ala Ser Asp Ser Asn Val Tyr Asp Leu Leu Lys Asp Leu Glu
130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
            165                 170                 175

His Asn Asp Asp Ala Leu Leu Lys Asn Tyr Gly Leu Leu Tyr Cys Phe
        180                 185                 190

Asn Ala Asp Met Ser Arg Val Ser Thr Phe Leu Arg Thr Val Gln Cys
    195                 200                 205

Arg Ser Val Glu Gly Ser Cys Gly Phe Gly Gly Gly Ser Gly Gly Gly
210                 215                 220

Gly Gly Ser Gly Gly Gly Gly Ser Gly Gly Gly Gly Ser Gly Gly Gly
225                 230                 235                 240

Gly Ser Phe Ser Gly Ser Glu Ala Thr Ala Ile Leu Ser Arg Ala
            245                 250                 255

Pro Trp Ser Leu Gln Ser Val Asn Pro Gly Leu Lys Thr Asn Ser Ser
        260                 265                 270

Lys Glu Pro Lys Phe Thr Lys Cys Arg Ser Pro Glu Arg Glu Thr Phe
    275                 280                 285

Ser Cys His Trp Thr Asp Glu Val His His Gly Thr Lys Asn Leu Gly
290                 295                 300

Pro Ile Gln Leu Phe Tyr Thr Arg Arg Asn Thr Gln Glu Trp Thr Gln
305                 310                 315                 320
```

```
Glu Trp Lys Glu Cys Pro Asp Tyr Val Ser Ala Gly Glu Asn Ser Cys
            325                 330                 335

Tyr Phe Asn Ser Ser Phe Thr Ser Ile Trp Ile Pro Tyr Cys Ile Lys
            340                 345                 350

Leu Thr Ser Asn Gly Gly Thr Val Asp Glu Lys Cys Phe Ser Val Asp
            355                 360                 365

Glu Ile Val Gln Pro Asp Pro Pro Ile Ala Leu Asn Trp Thr Leu Leu
            370                 375                 380

Asn Val Ser Leu Thr Gly Ile His Ala Asp Ile Gln Val Arg Trp Glu
385                 390                 395                 400

Ala Pro Arg Asn Ala Asp Ile Gln Lys Gly Trp Met Val Leu Glu Tyr
            405                 410                 415

Glu Leu Gln Tyr Lys Glu Val Asn Glu Thr Lys Trp Lys Met Met Asp
            420                 425                 430

Pro Ile Leu Thr Thr Ser Val Pro Val Tyr Ser Leu Lys Val Asp Lys
            435                 440                 445

Glu Tyr Glu Val Arg Val Arg Ser Lys Gln Arg Asn Ser Gly Asn Tyr
            450                 455                 460

Gly Glu Phe Ser Glu Val Leu Tyr Val Thr Leu Pro Gln Met Ser Gln
465                 470                 475                 480

<210> SEQ ID NO 32
<211> LENGTH: 455
<212> TYPE: PRT
<213> ORGANISM: Artificial
<220> FEATURE:
<223> OTHER INFORMATION: growth hormone fusion protein

<400> SEQUENCE: 32

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala Asp Arg Leu Asn Gln
            35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
            85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
            115                 120                 125

Tyr Gly Ala Ser Asp Ser Asn Val Tyr Asp Leu Leu Lys Asp Leu Glu
        130                 135                 140

Glu Arg Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
            165                 170                 175

His Asn Asp Asp Ala Leu Leu Lys Asn Tyr Gly Leu Leu Tyr Cys Phe
            180                 185                 190

Asn Ala Asp Met Ser Arg Val Ser Thr Phe Leu Arg Thr Val Gln Cys
            195                 200                 205
```

-continued

```
Arg Ser Val Glu Gly Ser Cys Gly Phe Phe Ser Gly Ser Glu Ala Thr
    210             215             220
Ala Ala Ile Leu Ser Arg Ala Pro Trp Ser Leu Gln Ser Val Asn Pro
225             230             235             240
Gly Leu Lys Thr Asn Ser Ser Lys Glu Pro Lys Phe Thr Lys Cys Arg
            245             250             255
Ser Pro Glu Arg Glu Thr Phe Ser Cys His Trp Thr Asp Glu Val His
            260             265             270
His Gly Thr Lys Asn Leu Gly Pro Ile Gln Leu Phe Tyr Thr Arg Arg
            275             280             285
Asn Thr Gln Glu Trp Thr Gln Glu Trp Lys Glu Cys Pro Asp Tyr Val
    290             295             300
Ser Ala Gly Glu Asn Ser Cys Tyr Phe Asn Ser Ser Phe Thr Ser Ile
305             310             315             320
Trp Ile Pro Tyr Cys Ile Lys Leu Thr Ser Asn Gly Gly Thr Val Asp
                325             330             335
Glu Lys Cys Phe Ser Val Asp Glu Ile Val Gln Pro Asp Pro Pro Ile
            340             345             350
Ala Leu Asn Trp Thr Leu Leu Asn Val Ser Leu Thr Gly Ile His Ala
            355             360             365
Asp Ile Gln Val Arg Trp Glu Ala Pro Arg Asn Ala Asp Ile Gln Lys
    370             375             380
Gly Trp Met Val Leu Glu Tyr Glu Leu Gln Tyr Lys Glu Val Asn Glu
385             390             395             400
Thr Lys Trp Lys Met Met Asp Pro Ile Leu Thr Thr Ser Val Pro Val
            405             410             415
Tyr Ser Leu Lys Val Asp Lys Glu Tyr Glu Val Arg Val Arg Ser Lys
            420             425             430
Gln Arg Asn Ser Gly Asn Tyr Gly Glu Phe Ser Glu Val Leu Tyr Val
            435             440             445
Thr Leu Pro Gln Met Ser Gln
    450             455
```

MODIFIED GROWTH HORMONE POLYPEPTIDES

CROSS REFERENCE TO RELATED APPLICATIONS

This is the U.S. national stage of PCT Application No. PCT/GB2008/003056, filed on Sep. 10, 2008, which was published in English under PCT Article 21(2). PCT Application No. PCT/GB2008/003056 claims the benefit of U.S. Provisional Application No. 60/979,010, filed on Oct. 10, 2007 and claims priority to Great Britain Patent Application No. GB 0719818.7, filed on Oct. 11, 2007.

The invention relates to modified growth hormone fusion proteins and dimers comprising said fusion proteins; nucleic acid molecules encoding said proteins and methods of treatment that use said proteins.

Growth hormone (GH) is an anabolic cytokine hormone important for linear growth in childhood and normal body composition in adults. The regulation of GH activity is complex and involves a number of interacting polypeptide and peptide agonists and antagonists. GH can mediate its effects either directly by binding growth hormone receptor or indirectly by stimulating production of Insulin-like growth factor-1 (IGF-1). A major role of GH is therefore the stimulation of the liver to produce IGF-1. In addition the secretion of GH is controlled by two peptide hormones with opposing activities. Growth hormone releasing hormone (GHRH) is a 44 amino acid peptide produced by the arcuate nucleus of the hypothalamus. It functions to stimulate GH production by the anterior pituitary gland. Somatostatin is a peptide hormone that opposes the effects of GHRH and is processed from a larger pre-propeptide to a 14 and 28 amino acid form. Somatostatin is secreted by neuroendocrine cells of the periventricular nucleus of the hypothalamus into the hypothalamo-hypophysial portal system that connects with the anterior pituitary gland where it inhibits secretion of GH.

GH binds sequentially with two membrane bound growth hormone receptors (GHR) via two separate sites on GH referred as site 1 and site 2. Site 1 is a high affinity binding site and site 2 a low affinity site. A single GH molecule binds 1 GHR via site 1. A second GHR is then recruited via site 2 to form a GHR:GH:GHR complex. The complex is then internalised and activates a signal transduction cascade leading to changes in gene expression. The extracellular domain of GHR exists as two linked domains each of approximately 100 amino acids (SD-100), the C-terminal SD-100 domain (b) being closest to the cell surface and the N-terminal SD-100 domain (a) being furthest away. It is a conformational change in these two domains that occurs on hormone binding with the formation of the trimeric complex GHR-GH-GHR.

GH excess is associated with a number of disease conditions; for example acromegaly and pituitary gigantism. Most cases of GH excess result from a pituitary tumour in the somatotroph cells of the anterior pituitary gland. These tumours are benign and gradually increase the secretion of GH. The symptoms of growth hormone excess include thickening of the bones of the jaw, fingers and toes, pressure on the nerves/muscles and insulin resistance. The original treatment for tumour related GH excess is the surgical removal of the pituitary tumour. Latterly, the use of GH antagonists to inhibit GH signalling is becoming the preferred treatment due to its non-invasive nature. GH antagonists can either be recombinant forms of somatostatin or somatostatin analogues (e.g. octreotide, lanreotide) or modified GH.

A review of modified GH antagonists is provided in Kopchick (2003) European Journal of Endocrinology 148; S21-25 which describes a commercially available GH antagonist called pegvisomant which combines a modification to human GH at G120 with the addition of polyethylene glycol to increase the molecular weight of modified GH. A problem associated with the administration of growth hormone is its rapid clearance by renal filtration and/or proteolysis. The addition of polyethylene glycol reduces this loss. However, it is known that polyethylene glycol reduces the affinity of GH for GHR and therefore to compensate for this reduced affinity it is necessary to administer elevated amounts of modified GH. This can result in side effects. It would be desirable to provide a modified GH antagonist that can be administered at reduced dosage thereby avoiding the problems associated with pegvisomant. This can be a reduction in either to amount administered or a reduction in the frequency of administration.

In our co-pending application WO03/070765 we describe modified GH fusion proteins that include modifications to site 1 and site 2 in GH. These modified GH molecules are fused to an extracellular domain of GHR. We herein disclose modified GH fusion proteins that have vastly extended serum half life and form dimers which may be related to the improved pharmacokinetics of these fusion proteins either by reducing renal clearance or protecting modified GH from proteolysis. The improved pharmacokinetic profiles of these growth hormone fusion proteins will allow treatment regimes that do not require multiple administrations and reduce undesirable side effects.

According to an aspect of the invention there is provided a nucleic acid molecule comprising a nucleic acid sequence selected from:

i) a nucleic acid sequence as represented in SEQ ID NO:1;
ii) a nucleic acid sequence as represented in SEQ ID NO:2;
iii) a nucleic acid sequence as represented in SEQ ID NO:4;
iv) a nucleic acid sequence as represented in SEQ ID NO:5;
v) a nucleic acid sequence as represented in SEQ ID NO:7;
vi) a nucleic acid sequence as represented in SEQ ID NO:8;
vii) a nucleic acid sequence as represented in SEQ ID NO:10;
viii) a nucleic acid sequence as represented in SEQ ID NO:11;
ix) a nucleic acid sequence as represented in SEQ ID NO:13;
x) a nucleic acid sequence as represented in SEQ ID NO:14;
xi) a nucleic acid sequence as represented in SEQ ID NO:16;
xii) a nucleic acid sequence as represented in SEQ ID NO:17;
xiii) a nucleic acid sequence as represented in SEQ ID NO:19;
xiv) a nucleic acid sequence as represented in SEQ ID NO:20;
xv) a nucleic acid sequence as represented in SEQ ID NO:22;
xvi) a nucleic acid sequence as represented in SEQ ID NO:23;
xvii) a nucleic acid molecule comprising a nucleic sequence that hybridizes under stringent hybridization conditions to SEQ ID NO:1, 2, 4, 5, 7, 8, 10, 11, 13, 14, 16, 17, 19, 20, 22 or 23 and which encodes a polypeptide that has growth hormone receptor antagonist activity.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, New York, 1993). The $T_m$ is the temperature at which 50% of a given strand of a nucleic acid molecule is hybridized to its complementary strand. The following is an exemplary set of hybridization conditions and is not limiting:

Very High Stringency (Allows Sequences that Share at Least 90% Identity to Hybridize)

| | |
|---|---|
| Hybridization: | 5× SSC at 65° C. for 16 hours |
| Wash twice: | 2× SSC at room temperature (RT) for 15 minutes each |
| Wash twice: | 0.5× SSC at 65° C. for 20 minutes each |

High Stringency (Allows Sequences that Share at Least 80% Identity to Hybridize)

| | |
|---|---|
| Hybridization: | 5×-6× SSC at 65° C.-70° C. for 16-20 hours |
| Wash twice: | 2× SSC at RT for 5-20 minutes each |
| Wash twice: | 1× SSC at 55° C.-70° C. for 30 minutes each |

Low Stringency (Allows Sequences that Share at Least 50% Identity to Hybridize)

| | |
|---|---|
| Hybridization: | 6× SSC at RT to 55° C. for 16-20 hours |
| Wash at least twice: | 2×-3× SSC at RT to 55° C. for 20-30 minutes each. |

In a preferred embodiment of the invention said nucleic acid molecule comprises or consists of a nucleic acid sequence as represented in SEQ ID NO: 1.

In a preferred embodiment of the invention said nucleic acid molecule comprises or consists of a nucleic acid sequence as represented in SEQ ID NO: 2.

In a preferred embodiment of the invention said nucleic acid molecule comprises or consists of a nucleic acid sequence as represented in SEQ ID NO: 4.

In a preferred embodiment of the invention said nucleic acid molecule comprises or consists of a nucleic acid sequence as represented in SEQ ID NO: 5.

In a preferred embodiment of the invention said nucleic acid molecule comprises or consists of a nucleic acid sequence as represented in SEQ ID NO: 7.

In a preferred embodiment of the invention said nucleic acid molecule comprises or consists of a nucleic acid sequence as represented in SEQ ID NO: 8.

In a preferred embodiment of the invention said nucleic acid molecule comprises or consists of a nucleic acid sequence as represented in SEQ ID NO: 10.

In a preferred embodiment of the invention said nucleic acid molecule comprises or consists of a nucleic acid sequence as represented in SEQ ID NO: 11.

In a preferred embodiment of the invention said nucleic acid molecule comprises or consists of a nucleic acid sequence as represented in SEQ ID NO: 13.

In a preferred embodiment of the invention said nucleic acid molecule comprises or consists of a nucleic acid sequence as represented in SEQ ID NO: 14.

In a preferred embodiment of the invention said nucleic acid molecule comprises or consists of a nucleic acid sequence as represented in SEQ ID NO: 16

In a preferred embodiment of the invention said nucleic acid molecule comprises or consists of a nucleic acid sequence as represented in SEQ ID NO: 17.

In a preferred embodiment of the invention said nucleic acid molecule comprises or consists of a nucleic acid sequence as represented in SEQ ID NO: 19.

In a preferred embodiment of the invention said nucleic acid molecule comprises or consists of a nucleic acid sequence as represented in SEQ ID NO: 20.

In a preferred embodiment of the invention said nucleic acid molecule comprises or consists of a nucleic acid sequence as represented in SEQ ID NO: 22.

In a preferred embodiment of the invention said nucleic acid molecule comprises or consists of a nucleic acid sequence as represented in SEQ ID NO: 23.

According to an aspect of the invention there is provided a polypeptide encoded by the nucleic acid according to the invention.

According to a further aspect of the invention there is provided a polypeptide comprising an amino acid sequence selected from:

i) an amino acid sequence as represented in SEQ ID NO:3;
ii) an amino acid sequence as represented in SEQ ID NO:6;
iii) an amino acid sequence as represented in SEQ ID NO:9;
iv) an amino acid sequence as represented in SEQ ID NO:12;
v) an amino acid sequence as represented in SEQ ID NO:15;
vi) an amino acid sequence as represented in SEQ ID NO:18;
vii) an amino acid sequence as represented in SEQ ID NO: 21;
viii) an amino acid sequence as represented in SEQ ID NO:24;
ix) an amino acid sequence as represented in SEQ ID NO:25;
x) an amino acid sequence as represented in SEQ ID NO:26;
xi) an amino acid sequence as represented in SEQ ID NO: 27;
xii) an amino acid sequence as represented in SEQ ID NO:28;
xiii) an amino acid sequence as represented in SEQ ID NO:29;
xiv) an amino acid sequence as represented in SEQ ID NO:30;
xv) an amino acid sequence as represented in SEQ ID NO:31;
xvi) an amino acid sequence as represented in SEQ ID NO:32; wherein said polypeptide has growth hormone receptor antagonistt activity.

In a preferred embodiment of the invention said polypeptide comprises or consists of an amino acid sequence as represented in SEQ ID NO: 3.

In a preferred embodiment of the invention said polypeptide comprises or consists of an amino acid sequence as represented in SEQ ID NO: 6.

In a preferred embodiment of the invention said polypeptide comprises or consists of an amino acid sequence as represented in SEQ ID NO: 9.

In a preferred embodiment of the invention said polypeptide comprises or consists of an amino acid sequence as represented in SEQ ID NO: 12.

In a preferred embodiment of the invention said polypeptide comprises or consists of an amino acid sequence as represented in SEQ ID NO: 15.

In a preferred embodiment of the invention said polypeptide comprises or consists of an amino acid sequence as represented in SEQ ID NO: 18.

In a preferred embodiment of the invention said polypeptide comprises or consists of an amino acid sequence as represented in SEQ ID NO: 21.

In a preferred embodiment of the invention said polypeptide comprises or consists of an amino acid sequence as represented in SEQ ID NO: 24.

In a preferred embodiment of the invention said polypeptide comprises or consists of an amino acid sequence as represented in SEQ ID NO: 25.

In a preferred embodiment of the invention said polypeptide comprises or consists of an amino acid sequence as represented in SEQ ID NO: 26.

In a preferred embodiment of the invention said polypeptide comprises or consists of an amino acid sequence as represented in SEQ ID NO: 27.

In a preferred embodiment of the invention said polypeptide comprises or consists of an amino acid sequence as represented in SEQ ID NO: 28.

In a preferred embodiment of the invention said polypeptide comprises or consists of an amino acid sequence as represented in SEQ ID NO: 29.

In a preferred embodiment of the invention said polypeptide comprises or consists of an amino acid sequence as represented in SEQ ID NO: 30.

In a preferred embodiment of the invention said polypeptide comprises or consists of an amino acid sequence as represented in SEQ ID NO: 31.

In a preferred embodiment of the invention said polypeptide comprises or consists of an amino acid sequence as represented in SEQ ID NO: 32.

According to a further aspect of the invention there is provided a homodimer comprising two polypeptides comprising or consisting of SEQ ID NO: 3.

According to a further aspect of the invention there is provided a homodimer comprising two polypeptides comprising or consisting of SEQ ID NO: 6.

According to a further aspect of the invention there is provided a homodimer comprising two polypeptides comprising or consisting of SEQ ID NO: 9.

According to a further aspect of the invention there is provided a homodimer comprising two polypeptides comprising or consisting of SEQ ID NO: 12.

According to a further aspect of the invention there is provided a homodimer comprising two polypeptides comprising or consisting of SEQ ID NO: 15.

According to a further aspect of the invention there is provided a homodimer comprising two polypeptides comprising or consisting of SEQ ID NO: 18.

According to a further aspect of the invention there is provided a homodimer comprising two polypeptides comprising or consisting of SEQ ID NO: 21.

According to a further aspect of the invention there is provided a homodimer comprising two polypeptides comprising or consisting of SEQ ID NO: 24.

According to a further aspect of the invention there is provided a homodimer comprising two polypeptides comprising or consisting of SEQ ID NO: 25.

According to a further aspect of the invention there is provided a homodimer comprising two polypeptides comprising or consisting of SEQ ID NO: 26.

According to a further aspect of the invention there is provided a homodimer comprising two polypeptides comprising or consisting of SEQ ID NO: 27.

According to a further aspect of the invention there is provided a homodimer comprising two polypeptides comprising or consisting of SEQ ID NO: 28.

According to a further aspect of the invention there is provided a homodimer comprising two polypeptides comprising or consisting of SEQ ID NO: 29.

According to a further aspect of the invention there is provided a homodimer comprising two polypeptides comprising or consisting of SEQ ID NO: 30.

According to a further aspect of the invention there is provided a homodimer comprising two polypeptides comprising or consisting of SEQ ID NO: 31.

According to a further aspect of the invention there is provided a homodimer comprising two polypeptides comprising or consisting of SEQ ID NO: 32.

According to a further aspect of the invention there is provided a vector comprising a nucleic acid molecule according to the invention.

In a preferred embodiment of the invention said vector is an expression vector adapted to express the nucleic acid molecule according to the invention.

A vector including nucleic acid (s) according to the invention need not include a promoter or other regulatory sequence, particularly if the vector is to be used to introduce the nucleic acid into cells for recombination into the genome for stable transfection. Preferably the nucleic acid in the vector is operably linked to an appropriate promoter or other regulatory elements for transcription in a host cell. The vector may be a bi-functional expression vector which functions in multiple hosts. By "promoter" is meant a nucleotide sequence upstream from the transcriptional initiation site and which contains all the regulatory regions required for transcription. Suitable promoters include constitutive, tissue-specific, inducible, developmental or other promoters for expression in eukaryotic or prokaryotic cells. "Operably linked" means joined as part of the same nucleic acid molecule, suitably positioned and oriented for transcription to be initiated from the promoter. DNA operably linked to a promoter is "under transcriptional initiation regulation" of the promoter.

In a preferred embodiment the promoter is a constitutive, an inducible or regulatable promoter.

According to a further aspect of the invention there is provided a cell transfected or transformed with a nucleic acid molecule or vector according to the invention.

Preferably said cell is a eukaryotic cell. Alternatively said cell is a prokaryotic cell.

In a preferred embodiment of the invention said cell is selected from the group consisting of; a fungal cell (e.g. *Pichia* spp, *Saccharomyces* spp, *Neurospora* spp); insect cell (e.g. *Spodoptera* spp); a mammalian cell (e.g. COS cell, CHO cell); a plant cell.

According to a further aspect of the invention there is provided a pharmaceutical composition comprising a polypeptide according to the invention including an excipient or carrier.

In a preferred embodiment of the invention said pharmaceutical composition is combined with a further therapeutic agent.

When administered the pharmaceutical composition of the present invention is administered in pharmaceutically acceptable preparations. Such preparations may routinely contain pharmaceutically acceptable concentrations of salt, buffering agents, preservatives, compatible carriers, and optionally other therapeutic agents.

The pharmaceutical compositions of the invention can be administered by any conventional route, including injection. The administration and application may, for example, be oral, intravenous, intraperitoneal, intramuscular, intracavity, intra-articuar, subcutaneous, topical (eyes), dermal (e.g a cream lipid soluble insert into skin or mucus membrane), transdermal, or intranasal.

Pharmaceutical compositions of the invention are administered in effective amounts. An "effective amount" is that amount of pharmaceuticals/compositions that alone, or together with further doses or synergistic drugs, produces the desired response. This may involve only slowing the progression of the disease temporarily, although more preferably, it involves halting the progression of the disease permanently. This can be monitored by routine methods or can be monitored according to diagnostic methods.

The doses of the pharmaceuticals compositions administered to a subject can be chosen in accordance with different parameters, in particular in accordance with the mode of administration used and the state of the subject (i.e. age, sex). When administered, the pharmaceutical compositions of the invention are applied in pharmaceutically-acceptable amounts and in pharmaceutically-acceptable compositions. When used in medicine salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The pharmaceutical compositions may be combined, if desired, with a pharmaceutically-acceptable carrier. The term "pharmaceutically-acceptable carrier" as used herein means one or more compatible solid or liquid fillers, diluents or encapsulating substances that are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction that would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier that constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as syrup, elixir or an emulsion.

Compositions suitable for parenteral administration conveniently comprise a sterile aqueous or non-aqueous preparation that is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1, 3-butane diol. Among the acceptable solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

According to a further aspect of the invention there is provided a method to treat a human subject suffering from growth hormone excess comprising administering an effective amount of at least one polypeptide according to the invention.

In a preferred method of the invention said polypeptide is administered intravenously.

In an alternative preferred method of the invention said polypeptide is administered subcutaneously.

In a further preferred method of the invention said polypeptide is administered daily or at two day intervals; preferably said polypeptide is administered at weekly, 2 weekly or monthly intervals.

In a preferred method of the invention said growth hormone excess results in acromegaly.

In a preferred method of the invention said growth hormone excess results in gigantism.

According to a further aspect of the invention there is provided a method to treat a human subject suffering from cancer comprising administering an effective amount of at least one polypeptide according to the invention.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting, for example, lung, breast, thyroid, lymphoid, gastrointestinal, and genito-urinary tract, as well as adenocarcinomas which include malignancies such as most colon cancers, renal-cell carcinoma, prostate cancer and/or testicular tumours, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumours composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In a preferred method of the invention said cancer is prostate cancer.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following figures:

FIG. 1A 1B8v0: Consists of GH (contains site 1 mutation) linked to GHR extracellular (domains 1 and 2) via a G4Sx4 linker: this construct contains restriction enzyme sites around the linker region and at the 3' end; FIG. 1B is the encoded amino acid sequence;

FIG. 2A 1B8v1: This molecule is derived from 1B8v0 but contains no extraneous sequence at the 5' and 3' termini and contains a G4Sx4 linker; FIG. 2B is the encoded amino acid sequence;

FIG. 3A 1B8v2: This molecule is derived from 1B8v0 but contains no extraneous sequence and contains a G4Sx5 linker; FIG. 3B is the encoded amino acid sequence;

FIG. 4A 1B8v3: This molecule is derived from 1B8v0 but contains no extraneous sequence and contains no linker; FIG. 4B is the encoded amino acid sequence;

FIG. 5A 1B9v0: Consists of GH (contains site 1 and site 2 mutations) linked to GHR (domains 1 and 2) via a G4Sx4 linker: this construct contains restriction enzyme sites around the linker region and at the 3' end; FIG. 5B is the encoded amino acid sequence;

FIG. 6A 1B9v1: This molecule is derived from 1B9v0 but contains no extraneous sequence at the 5' and 3' termini and contains a G4Sx4 linker; FIG. 6B is the encoded amino acid sequence;

FIG. 7A 1B9v2: This molecule is derived from 1B9v0 but contains no extraneous sequence and contains a G4Sx5 linker; FIG. 7B is the encoded amino acid sequence;

FIG. 8A 1B9v3: This molecule is derived from 1B9v0 but contains no extraneous sequence and contains no linker; FIG. 8B is the encoded amino acid sequence;

Figure 13:
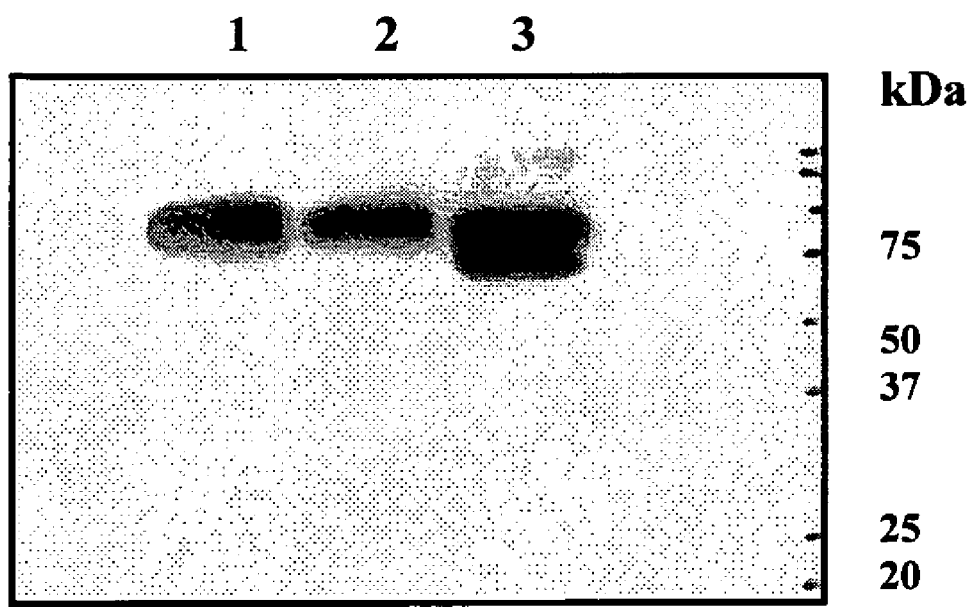
Figure 14:
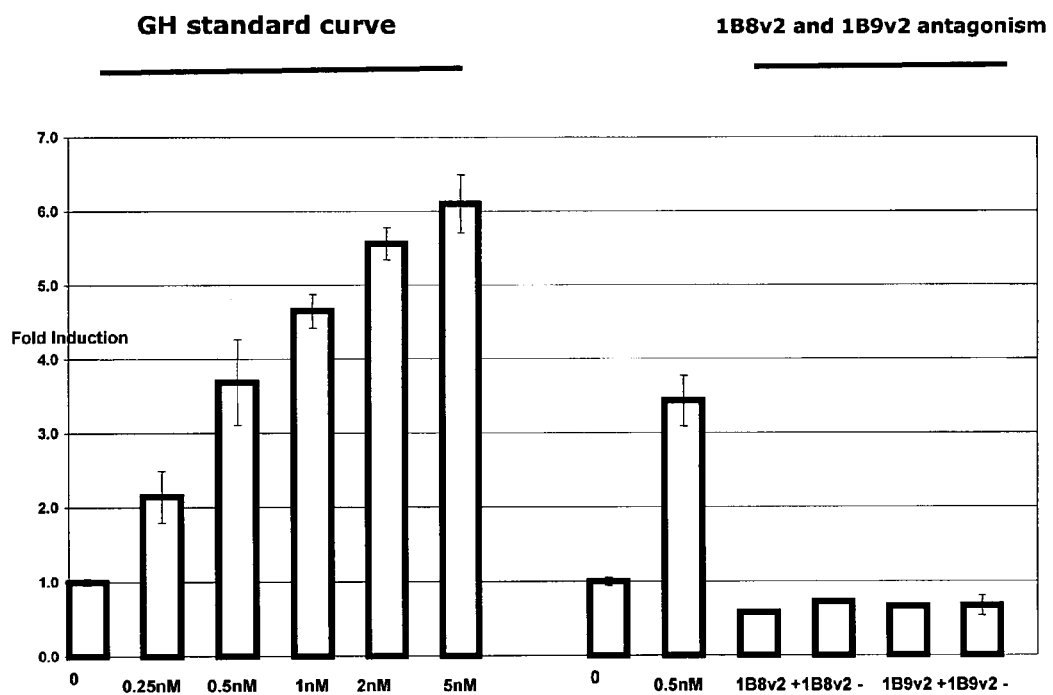
Figure 15A:
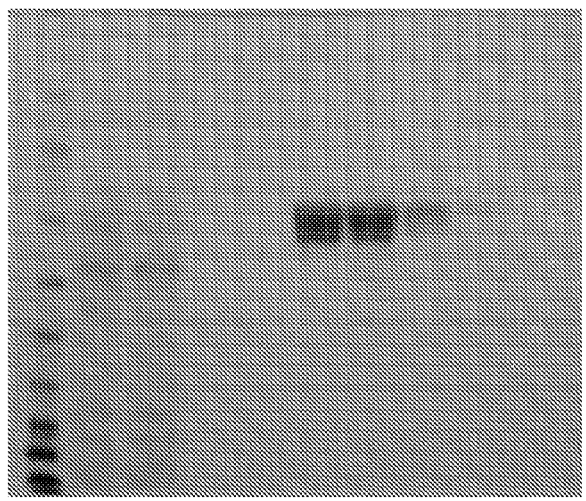
Figure 15B:
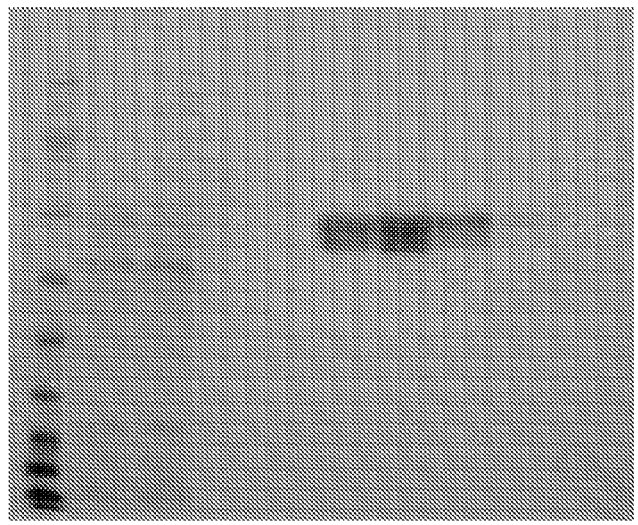
Figure 16A:
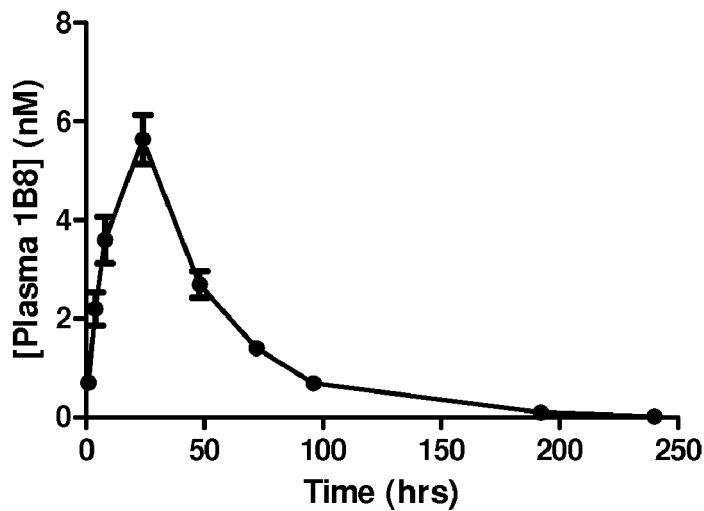
Figure 16B:
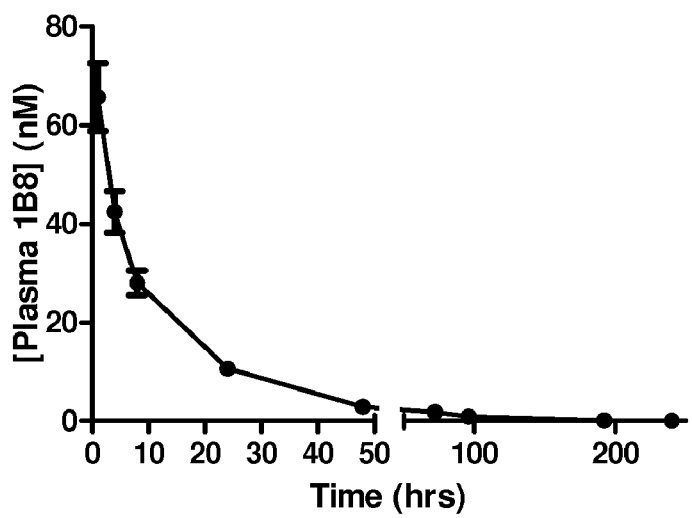
Figure 17A:
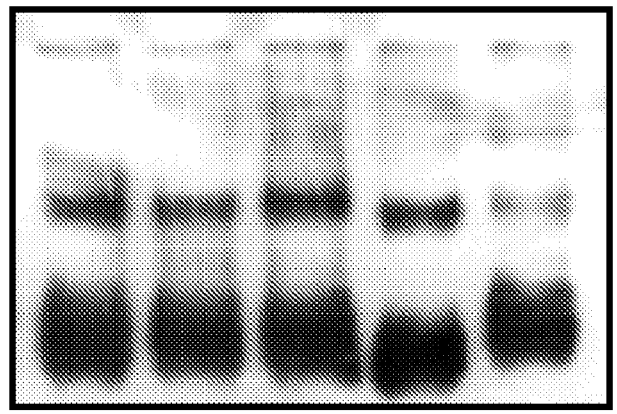
Figure 17B:
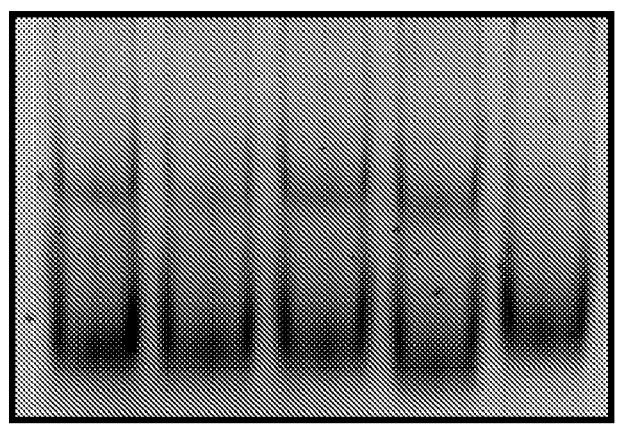
Figure 18:
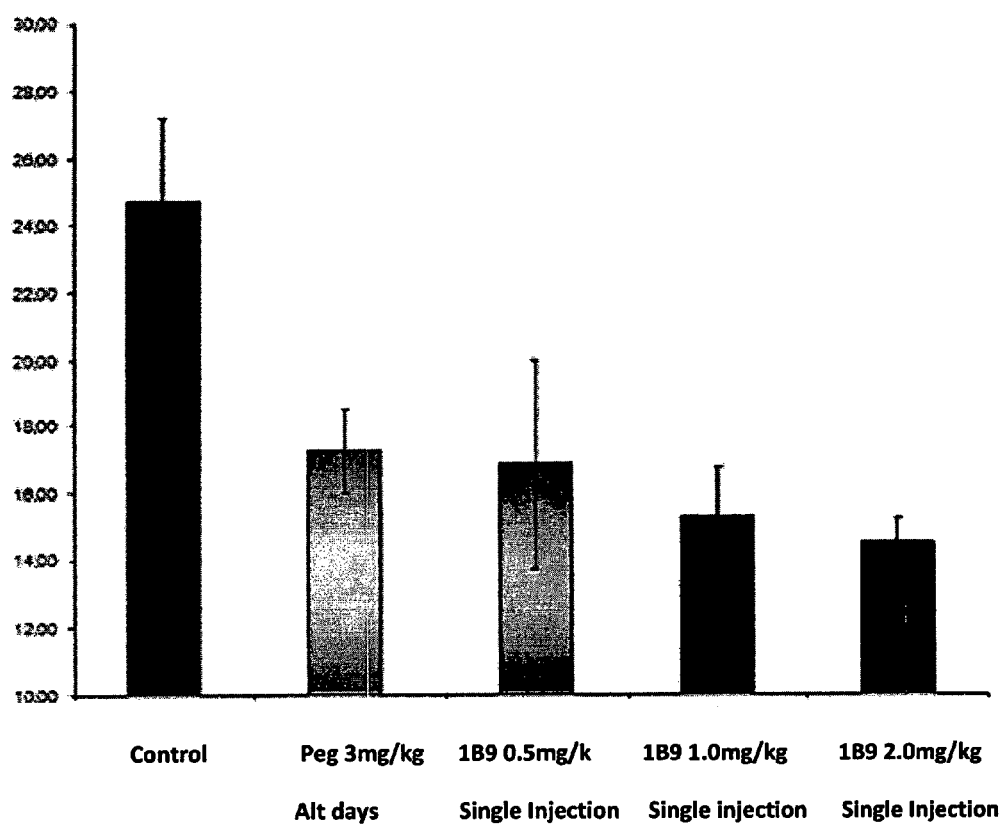
Figure 19:
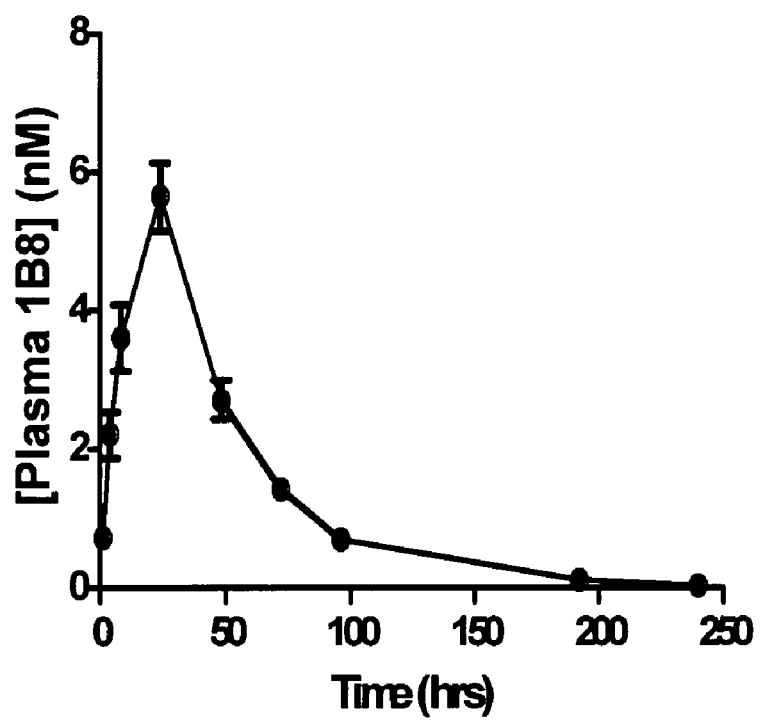

FIG. 11 illustrates 1B8 v2 fragment: Nar1-AvrII (524 bp). New linker region is shown in bold, with restriction enzyme site underlined. This fragment was ligated to the plasmid pGHsecTag-1 B8v1 to produce the plasmid, pGHsecTag-1B8v2;

FIG. 12: illustrates 1B9 v2 fragment: Nar1-AvrII (524 bp). New linker region is shown in bold, with restriction enzyme site underlined. This fragment was ligated to the plasmid pGHsecTag-1 B9v1 to produce the plasmid, pGHsecTag-1B9v2;

FIG. 13 shows a Western blot using a GH specific antibody to detect expression of both 1B8v2 (lanes 1 and 2) and 1B9v2 (lane 3) from cell culture media of a stable CHO Flp-In cell line. Samples are of correct size expected for each protein (~75 kDa) and show no signs of degradation;

FIG. 14 illustrates that in the presence (+) of 0.5 nM rhGH, media samples from both 1B8v2 and 1B9v2 stable cell lines are able to antagonise the actions of rhGH. In the absence (−) of 0.5 nM GH both molecules show no bioactivity. The standard curve for GH is shown (0-5 nM);

FIG. 15A shows SDS-PAGE analysis of purified protein fractions by coomassie staining. Image shows that purified protein (IB8v2) is of correct size expected (~75kDa) and that no lower molecular weight degraded products are visible; FIG. 15B shows SDS-PAGE analysis of IB9v2;

FIG. 16A After SC administration 1B8 serum protein levels peak at 24hrs post injection. 1B8 can still be detected 10 days post administration; FIG. 16B After IV administration 1B8 serum protein levels peak at 1hr post injection and then decline sharply;

FIG. 17A Western blot of Native-PAGE samples: 1; 1B7v0 native GH fusion, 2: 1B7v1 native GH, 3: 1B7v2 native GH, 4:1B7v3 native GH, 5: 1B8 modified GH fusion. All samples show a distinct double band, characteristic of a monomer and dimer formation; FIG. 17B the equivalent coomassie stained gel illustrating dimer foiination;

FIG. 18 illustrates % weight gain in NZ white rabbits over 12 days comparing 5 doses of pegvisomant administered with single doses of IB8 and IB9; and FIG. 19 illustrates PK of IB8 in NZ white rabbits over 250 hrs.

FIG. 20A is Table 1a and FIG. 20B is Table 1b. These two tables illustrate a Bradford Assay of 1B8v2 fractions.

MATERIALS AND METHODS

Construction of 1B8 Antagonist Molecule

The molecule has been constructed to mutate amino acid glycine-120 to arginine in the site 2 (low affinity site) of the GH molecule (G120R). Binding of the GH molecule to the GH receptor via the high affinity site 1 is unaffected, however binding to the receptor via GH site 2 is inhibited by the bulky side group of the arginine molecule.

A PCR strategy was previously employed to generate a GH molecule containing the G120R mutation and by the use of suitable restriction sites allowed the cloning of this molecule into the pTrc-His expression plasmid to produce the clone pTrc-His-1A7 (G120R linked to the GHR extracellular B domain).

Figure 9:
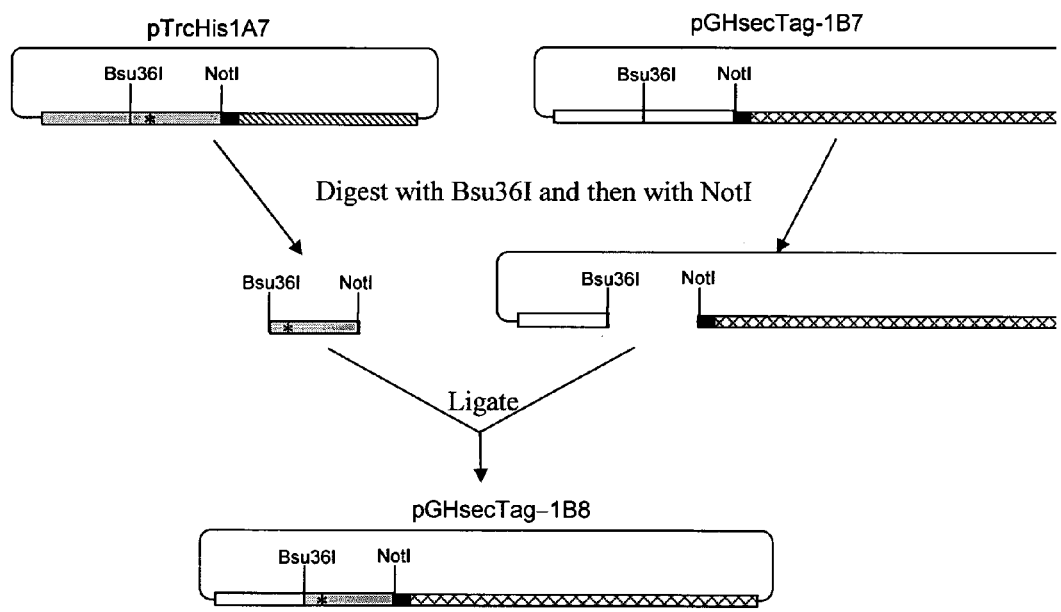
FIG. 9 illustrates the basic ligation strategy for subcloning the G120R molecule into a mammalian expression plasmid.

A 300 bp Bsu36I-Not 1 fragment was then excised from this vector and ligated into the mammalian expression plasmid pGHsecTag-1B7 (GH linked to the GHR extracellular domains A and B) to produce pGHsecTag-1B8 (secreted expression is directed by the GH secretion signal). See FIG. 9

Construction of 1B9v0 Antagonist Molecule

The molecule has been constructed to mutate amino acids in both site 1 and site 2 of the GH molecule. Binding of the GH molecule to the GH receptor via the high affinity site 1 is enhanced by these mutations, whereas binding to the receptor via GH site 2 is inhibited by a single glycine to arginine change.

Figure 10:
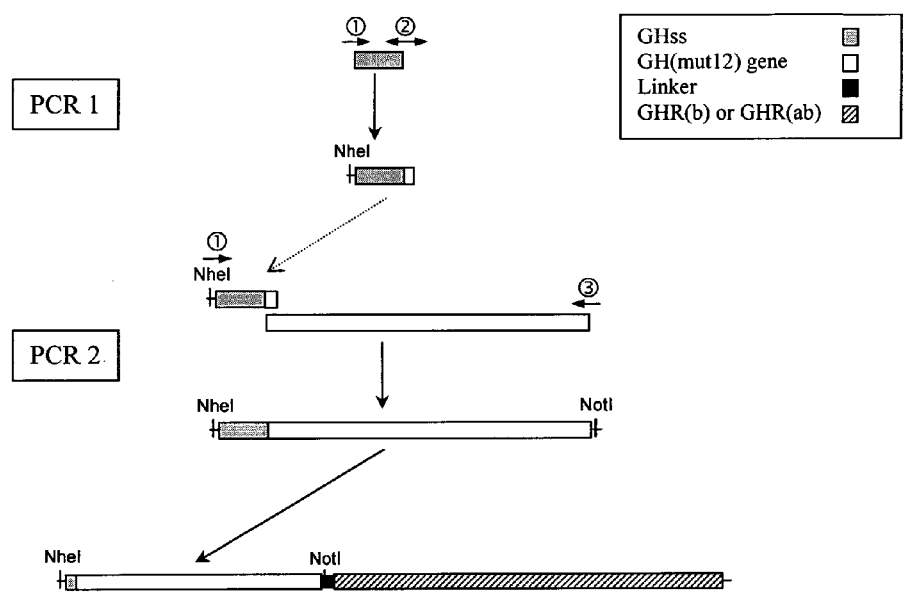
FIG. 10 illustrates the construction of IB9v0.

A single-strand DNA site directed mutation strategy was employed to generate a GH molecule containing both site 1 and site 2 mutations. The use of suitable restriction sites allowed the cloning of this molecule into the pTrc-His and pET21a (+) expression plasmids. Using PCR, a clone was generated that contained the GH signal sequence (GHss) with flanking Nhe1 and Not1 sites. This was ligated into the mammalian expression plasmid pGHsecTag-1B8v0 (GH linked to the GHR extracellular domains A and B) to produce pGHsec-Tag-1B9v0 (secreted expression is directed by the GH secretion signal). See FIG. 10.

Construction of the Variant Clones of Both 1B8V0 and 1B9V0

The plasmid pGHsecTag-1B7v3 was digested using the restriction enzymes HindIII-EcoRV and the fragment ligated into the plasmids pGHsecTag-1B8v0 and 1B9v0 to construct the plasmids pGHsecTag-1B8v1 and 1B9v1 (these molecules do not contain any erroneous sequence at the 3 prime end). The next stage was to remove restriction sites around the linker region to produce the plasmids pGHseTag-1B8v2 and 1B9v2. This was completed using gene synthesis and in which the original linker was replaced with a G4Sx5 linker.

The following fragments were constructed by Gene synthesis with flanking restriction sites, NarI and AvrII and ligated to either pGHsecTag-1B8v1 or 1B9v1; see FIGS. 11 and 12.

In Vitro Bioactivity of Antagonist Variant Molecules

The in vitro bioactivity of each chimera was tested using a GH-specific luciferase reporter assay. Essentially a human derived cell line was stably transfected with the human GH receptor and then transiently transfected with a luciferase signaling reporter. This assay detects physiological levels of GH, see FIG. 14.

Purification of Antagonist Molecules

CHO Flp-In cell lines expressing both 1B8v2 and 1B9v2 as a secreted product were grown in protein free media. Media was harvested, concentrated and clarified prior to affinity purification. For purification, a 20 ml NHS-activated Sepharose 4 Fast Flow resin coupled to 5E1 monoclonal antibody to hGH was prepared. Typically the media sample was concentrated ten fold and diluted 1:1 with Binding Buffer (25 mM Tris HCl/150 mM NaCl, pH 7.4) prior to purification.

Material was loaded onto the column at a flow rate of 2 ml/min. After washing, bound protein was eluted at 1 ml/min with 200 mM Glycine, pH 2.7 followed by neutralization with 1M Tris HCl, pH 9.0. Samples were analysed by SDS-PAGE (see FIGS. 15a and 15b). FIGS. 17a and 17b illustrate dimer formation of 1B9 compared to native growth hormone chimeras.

Pharmacokinetic Studies of IB8

6 normal healthy rats were given a single dose injection of 1 nMol (75 ug) of protein, either subcutaneous (SC, FIG. 16a) or intravenous (IV, FIG. 16b). Control rats were given vehicle only. Samples were taken at time intervals over the course of a 10 day period and assayed for the presence of 1B8 using an in-house GH Elisa assay.

TABLE 1a

|  | [protein] (µg/ml) | Volume (ml) | Total protein (mg) |
| --- | --- | --- | --- |
| 1B8v2 load | 293 | 106 | 31.1 |
| Unbound | 227 | 120 | 27.2 |
| Wash | — | 120 | — |
| Elution 1 | — | 5 | — |
| Elution 2 | 60.7 | 5 | 0.3 |
| Elution 3 | 63.6 | 5 | 0.32 |
| Elution 4 | 84.7 | 5 | 0.42 |
| Elution 5 | 18.5 | 5 | 0.09 |
| Elution 6 | 10.0 | 5 | 0.05 |
| 30 kDa F/T | 8.6 | 450 | 3.9 |

TABLE 1b

|  | [protein] (µg/ml) | Volume (ml) | Total protein (mg) |
| --- | --- | --- | --- |
| 1B9v2 load | 311 | 110 | 34.2 |
| Unbound | 246 | 125 | 30.8 |
| Wash | — | 150 | — |
| Elution 1 | 9.4 | 5 | — |
| Elution 2 | 32.4 | 5 | 0.16 |
| Elution 3 | 129 | 5 | 0.65 |
| Elution 4 | 80.1 | 5 | 0.4 |
| Elution 5 | 37.1 | 5 | 0.19 |
| Elution 6 | 9.4 | 5 | 0.05 |
| 30 kDa F/T | 9.4 | 450 |  |

The invention claimed is:

1. An isolated nucleic acid molecule comprising a nucleic acid sequence selected from the group consisting of: the nucleic acid sequence set forth as SEQ ID NO:22; and the nucleic acid sequence set forth as SEQ ID NO:23.

2. A vector comprising the nucleic acid molecule according to claim 1.

3. An isolated host cell transfected or transformed with a vector according to claim 2.

4. An isolated polypeptide encoded by an isolated nucleic acid molecule comprising the nucleic acid sequence set forth as SEQ ID NO: 22 or SEQ ID NO: 23.

5. A pharmaceutical composition comprising a polypeptide according to claim 4, and an excipient or a carrier.

6. A composition according to claim 5, comprising a further therapeutic agent.

7. A method to treat a human subject suffering from growth hormone excess comprising
administering to the human subject an effective amount of the polypeptide of claim 4, thereby treating the growth hormone excess in the human subject.

8. The method according to claim 7, wherein said polypeptide is administered intravenously.

9. The method according to claim 7, wherein said polypeptide is administered subcutaneously.

10. The method according to claim 7, wherein said polypeptide is administered daily or at two day intervals.

11. The method according to claim 7, wherein said polypeptide is administered at weekly intervals.

12. The method according to claim 7, wherein said polypeptide is administered at bi-weekly intervals.

13. The method according to claim 7, wherein said polypeptide is administered at monthly intervals.

14. The method according to claim 7, wherein said growth hormone excess results in acromegaly.

15. The method according claim 7, wherein said growth hormone excess results in gigantism.

16. A method to treat a human subject suffering from cancer associated with excess growth hormone activity comprising administering to the human subject an effective amount of at least one polypeptide according to claim 4, thereby treating the cancer in the human subject.

17. The method according to claim 16, wherein the cancer is prostate cancer.

18. An isolated polypeptide comprising an amino acid sequence selected from the group consisting of: the amino acid sequence set forth as SEQ ID NO:24; and the amino acid sequence set forth as SEQ ID NO:32.

19. The isolated polypeptide of claim 18, comprising the amino acid sequence set forth as SEQ ID NO: 32.

20. A homodimer comprising two identical polypeptides, wherein each of the two polypeptides comprises the amino acid sequence set forth as SEQ ID NO: 24 ; or SEQ ID NO: 32.

21. An isolated polynucleotide encoding a polypeptide comprising the amino acid sequence set forth as SEQ ID NO:32.

22. The isolated polynucleotide of claim 21, comprising the polynucleotide sequence set forth as SEQ ID NO: 22.

* * * * *